United States Patent
Ota et al.

(10) Patent No.: US 10,847,725 B2
(45) Date of Patent: *Nov. 24, 2020

(54) SULFONIC ACID ESTER COMPOUND AND USE THEREFOR

(71) Applicant: NISSAN CHEMICAL CORPORATION, Tokyo (JP)

(72) Inventors: Hirofumi Ota, Funabashi (JP); Toshiyuki Endo, Funabashi (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 67 days.

This patent is subject to a terminal disclaimer.

(21) Appl. No.: 16/309,866

(22) PCT Filed: Jun. 14, 2017

(86) PCT No.: PCT/JP2017/021968
§ 371 (c)(1),
(2) Date: Dec. 13, 2018

(87) PCT Pub. No.: WO2017/217455
PCT Pub. Date: Dec. 21, 2017

(65) Prior Publication Data
US 2019/0140183 A1 May 9, 2019

(30) Foreign Application Priority Data

Jun. 16, 2016 (JP) ................................. 2016-119809

(51) Int. Cl.
| C07C 309/75 | (2006.01) |
| H01L 51/50 | (2006.01) |
| C09D 201/00 | (2006.01) |
| C09K 11/06 | (2006.01) |
| C08L 81/08 | (2006.01) |
| H01L 51/00 | (2006.01) |

(52) U.S. Cl.
CPC ........ H01L 51/0051 (2013.01); C07C 309/75 (2013.01); C08L 81/08 (2013.01); C09D 201/00 (2013.01); C09K 11/06 (2013.01); H01L 51/0007 (2013.01); H01L 51/50 (2013.01); C08L 2203/20 (2013.01)

(58) Field of Classification Search
CPC .................................................. H01L 51/0051
See application file for complete search history.

(56) References Cited

U.S. PATENT DOCUMENTS

| 4,597,891 A * | 7/1986 | Rogers ................... C09K 19/60 252/299.1 |
| 4,599,350 A * | 7/1986 | Gayer .................... A01N 43/10 514/444 |
| 5,378,571 A * | 1/1995 | Macholdt ........... G03G 9/09741 430/108.2 |
| 6,635,400 B2 * | 10/2003 | Kato ...................... G03F 7/0233 430/170 |
| 9,146,467 B2 * | 9/2015 | Houlihan ............... C07C 307/02 |
| 10,513,491 B2 * | 12/2019 | Ota ......................... H01L 51/50 |
| 2004/0158093 A1 * | 8/2004 | Ueda ...................... C07C 271/22 558/411 |
| 2006/0115652 A1 | 6/2006 | Yoshimoto et al. |
| 2007/0043222 A1 | 2/2007 | Yoshimoto et al. |
| 2007/0105030 A1 | 5/2007 | Yoshimoto et al. |
| 2008/0269345 A1 * | 10/2008 | Takagaki .................. A61P 9/10 514/643 |
| 2017/0104161 A1 | 4/2017 | Otani |

FOREIGN PATENT DOCUMENTS

| JP | 7-134416 A | 5/1995 |
| JP | 2002-151272 A | 5/2002 |
| JP | 5136795 B2 | 2/2013 |
| JP | 2015-213147 A | 11/2015 |

(Continued)

OTHER PUBLICATIONS

"Chemical Reactions Exhibiting Proliferation of Catalytic Molecules", Kino Zairyo, 2004, vol. 24, pp. 72-82.
International Search Report (PCT/ISA/210) issued in PCT/JP2017/021968, dated Sep. 5, 2017.
Nenitzescu et al., "Über Die Alkylierung Des Aromatischen Kerns Mit Sulfonsäureestern", Chemische Berichte, 1957, vol. 90, pp. 585-592.

(Continued)

*Primary Examiner* — William A Harriston
(74) *Attorney, Agent, or Firm* — Birch, Stewart, Kolasch & Birch, LLP

(57) ABSTRACT

Provided is an electron-accepting substance precursor comprising a sulfonic acid ester compound represented by formula (1).

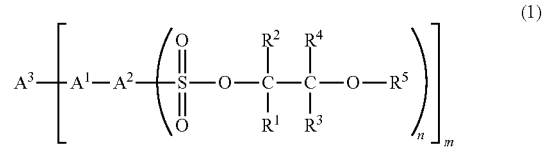

(In the formula, $R^1$-$R^4$ each independently represent a hydrogen atom, or a straight-chain or branched C1-6 alkyl group. $R^5$ represents a C2-20 monovalent hydrocarbon group which may be substituted. $A^1$ represents —O— or —S—. $A^2$ represents a group having a valence of (n+1) and derived from naphthalene or anthracene. $A^3$ represents a group having a valence of m and derived from perfluorinated biphenyl. m represents an integer satisfying 2≤m≤4. n represents an integer satisfying 1≤n≤4).

11 Claims, No Drawings

(56) References Cited

FOREIGN PATENT DOCUMENTS

| WO | WO 2004/043117 A1 | 5/2004 |
| WO | WO 2005/000832 A1 | 1/2005 |
| WO | WO 2005/043962 A1 | 5/2005 |
| WO | WO 2007/099808 A1 | 9/2007 |
| WO | WO 2015/186688 A1 | 12/2015 |

OTHER PUBLICATIONS

Written Opinion of the International Searching Authority (PCT/ISA/237) issued in PCT/JP2017/021968, dated Sep. 5, 2017.
U.S. Appl. No. 16/309,845, filed Dec. 13, 2018.

\* cited by examiner

SULFONIC ACID ESTER COMPOUND AND USE THEREFOR

TECHNICAL FIELD

The present invention relates to a sulfonic acid ester compound and uses therefor.

BACKGROUND ART

Charge-transporting thin films made of organic compounds are used as light-emitting layers and charge-injecting layers in organic electroluminescent (EL) devices. In particular, a hole-injecting layer is responsible for transferring charge between an anode and a hole-transporting layer or a light-emitting layer, and thus carries out an important function for achieving low-voltage driving and high brightness in organic EL devices.

In the past few years, charge-transporting varnishes composed of a uniform solution of a low-molecular-weight oligoaniline-based material or an oligothiophene-based material dissolved in an organic solvent have been discovered and it has been reported that, by inserting a hole-injecting layer obtained from such a varnish in an organic EL device, an underlying substrate leveling effect and excellent organic EL device properties can be obtained (Patent Documents 1 to 3). Moreover, it has also been reported that, by using a 1,4-benzodioxanesulfonic acid compound as an electron-accepting substance (Patent Document 4), the driving voltage of organic EL devices can be lowered.

Yet, because sulfonic acid compounds generally have a low solubility in organic solvents, there tend to be limitations on the solvent used when preparing an organic solution; that is, it has been necessary to include a highly polar organic solvent which has a high solvating power, such as N,N-dimethylacetamide or N-methylpyrrolidone. Organic solutions containing a highly polar organic solvent sometimes cause damage to parts of inkjet coating devices or to organic structures such as insulating films and barrier membranes formed on substrates. Another problem is that, with the prolonged atmospheric exposure of a varnish containing a highly polar organic solvent, the electrical conductivity of the varnish rises over time due to water absorption, as a result of which inkjet discharge becomes unstable. Moreover, because sulfonic acid compounds are highly polar, purification by silica gel column chromatography, liquid/liquid extraction, and salt removal by an operation such as water rinsing are difficult.

At the same time, sulfonic acid ester compounds are known to be materials which have a high solubility in various organic solvents and which generate strong organic acids under external stimulation such as heating or chemical action. The cyclohexyl ester of sulfonic acid has been reported as a specific example of a compound which generates sulfonic acid under heating (Non-Patent Document 1). Notice has also been taken of this sulfonic acid ester compound in terms of the concept of a thermal acid generator (Patent Document 5, Non-Patent Document 2). Yet, particularly with regard to sulfonic acid ester compounds substituted on the electron-deficient aromatic ring of an aromatic disulfonic acid or the like, there has existed a desire for the creation of highly stable sulfonic acid ester compounds that readily decompose under slight heating or via reaction with water, a basic substance or the like.

PRIOR ART DOCUMENTS

Patent Documents

Patent Document 1: JP-A 2002-151272
Patent Document 2: WO 2004/043117
Patent Document 3: WO 2005/043962
Patent Document 4: WO 2005/000832
Patent Document 5: JP-A H07-134416
Patent Document 6: JP No. 5136795
Non-Patent Document 1: *Chemische Berichte*, 90, pp. 585-592 (1957)
Non-Patent Document 2: *Kino Zairyo*, 24, pp. 72-82 (2004)

SUMMARY OF INVENTION

Technical Problem

The inventors, in order to resolve the above problems, have reported sulfonic acid ester compounds that possess a high stability and also have a high solubility in a wide range of organic solvents (Patent Document 6). However, although these sulfonic acid ester compounds have a better stability and a better solubility in organic solvents than the sulfonic acid compounds and sulfonic acid ester compounds that have hitherto been used, dissolving them in low-polarity solvents requires a high temperature and prolonged stirring. Moreover, when such compounds are formed into a solution, settling occurs with long-term storage. Hence, there has remained room for improvement, both in the solubility of these compounds in organic solvents and in their stability.

It is therefore an object of the invention to provide an electron-accepting substance precursor consisting of a sulfonic acid ester compound which has an excellent solubility in low-polarity solvents, which has an excellent stability as a varnish, and which, when employed in organic EL devices, makes it possible to achieve excellent device characteristics. A further object of the invention is to provide a charge-transporting varnish containing such a precursor.

Solution to Problem

The inventors have conducted extensive investigations in order to achieve the above object. As a result, they have discovered that esters of specific sulfonic acid compounds and glycol ethers have an excellent solubility in low-polarity solvents compared with conventional sulfonic acid ester compounds, and moreover, when rendered into solutions, also have an excellent shelf stability, enabling them to function as electron-accepting substance precursors.

Accordingly, the invention provides the following electron-accepting substance precursor and charge-transporting varnish.

1. An electron-accepting substance precursor consisting of a sulfonic acid ester compound of formula (1) below

[Chem. 1]

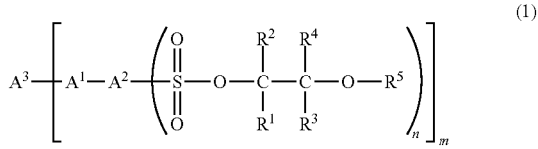

wherein $R^1$ to $R^4$ are each independently a hydrogen atom or a linear or branched alkyl group of 1 to 6 carbon atoms, and $R^5$ is a monovalent hydrocarbon group of 2 to 20 carbon atoms which may be substituted;

$A^1$ represents —O— or —S—, $A^2$ is a group having a valence of n+1 which is derived from naphthalene or anthracene, and A is an m-valent group derived from perfluorobiphenyl; and m is an integer that satisfies the condition 2≤m≤4, and n is an integer that satisfies the condition 1≤n≤4.

2. The electron-accepting substance precursor of 1 above, wherein $R^1$ or $R^3$ is a linear alkyl group of 1 to 3 carbon atoms and the remainder of $R^1$ to $R^4$ are hydrogen atoms.

3. The electron-accepting substance precursor of 2 above, wherein $R^1$ is a linear alkyl group of 1 to 3 carbon atoms and $R^2$ to $R^4$ are hydrogen atoms.

4. The electron-accepting substance precursor of any of 1 to 3 above, wherein $R^5$ is a linear alkyl group of 2 to 4 carbon atoms or a phenyl group.

5. The electron-accepting substance precursor of any of 1 to 4 above, wherein m is 2.

6. The electron-accepting substance precursor of any of 1 to 5 above, wherein n is 2.

7. A charge-transporting varnish comprising the electron-accepting substance precursor of any of 1 to 6 above, a charge-transporting substance and an organic solvent.

8. The charge-transporting varnish of 7 above, wherein the organic solvent is a low-polarity organic solvent.

9. The charge-transporting varnish of 7 or 8 above, wherein the charge-transporting substance is an aniline derivative.

10. A charge-transporting thin film produced using the charge-transporting varnish of any of 7 to 9 above.

11. An organic EL device comprising the charge-transporting thin film of 10 above.

Advantageous Effects of Invention

The electron-accepting substance precursor of the invention has a high solubility in a broad range of organic solvents, including low-polarity solvents. Therefore, a charge-transporting varnish can be prepared from this compound even when a low-polarity solvent is used or the proportion of high-polarity solvent is decreased. Moreover, when a solution of the compound is prepared, the shelf stability of the solution is also excellent. Not only can low-polarity organic solvent-based charge-transporting varnishes be applied with inkjet coaters, which have a poor solvent resistance, they can be used even in cases where a structure having a poor solvent resistance, such as an insulating film or a barrier membrane, is present on a substrate. As a result, amorphous solid thin-films having a high flatness can be produced without difficulty. In addition, low-polarity organic solvent-based charge-transporting varnishes lack water absorbing properties and therefore have a long-term atmospheric stability.

Also, because thin films obtained from the charge-transporting varnish of the invention have a high charge transportability, when such a film is used as a hole-injecting layer or a hole-transporting layer, the driving voltage of the organic EL device can be lowered. By taking advantage of the high flatness and high charge transportability of these thin films, it is also possible to employ the thin films as hole-transporting layers in solar cells, as fuel cell electrodes, as protective films for capacitor electrodes, and as antistatic films.

DESCRIPTION OF EMBODIMENTS

[Electron-Accepting Substance Precursor]

The electron-accepting substance precursor of the invention consists of a sulfonic acid ester compound of formula (1) below. In this invention, "electron-accepting substance" refers to a substance that can be used for enhancing the electron transporting ability and increasing the uniformity of film formation, and is synonymous with an electron-accepting dopant.

[Chem. 2]

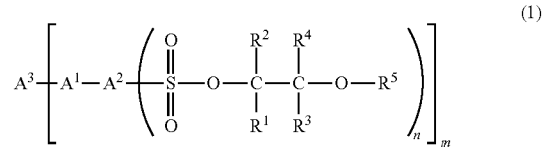

(1)

In formula (1), $R^1$ to $R^4$ are each independently a hydrogen atom or a linear or branched alkyl group of 1 to 6 carbon atoms; and $R^5$ is a monovalent hydrocarbon group of 2 to 20 carbon atoms which may be substituted.

Examples of the linear or branched alkyl groups include, without particular limitation, methyl, ethyl, n-propyl, isopropyl, n-butyl, isobutyl, tert-butyl and n-hexyl groups. Of these, an alkyl group of 1 to 3 carbon atoms is preferred.

Examples of monovalent hydrocarbon groups of 2 to 20 carbon atoms include alkyl groups such as ethyl, n-propyl, isopropyl, n-butyl, isobutyl and tert-butyl groups, and aryl groups such as phenyl, naphthyl and phenanthryl groups.

It is preferable for $R^1$ or $R^3$ to be a linear alkyl group of 1 to 3 carbon atoms and for the remainder of $R^1$ to $R^4$ to be hydrogen atoms. In addition, it is preferable for $R^1$ to be a linear alkyl group of 1 to 3 carbon atoms, and for $R^2$ to $R^4$ to be hydrogen atoms. The linear alkyl group of 1 to 3 carbon atoms is preferably a methyl group. $R^5$ is preferably a linear alkyl group of 2 to 4 carbon atoms or a phenyl group.

In formula (1), $A^1$ represents —O— or —S—, and is preferably —O—. $A^2$ is a group having a valence of n+1 which is derived from naphthalene or anthracene, and is preferably a group derived from naphthalene. $A^3$ is an m-valent group derived from perfluorobiphenyl.

In formula (1), m is an integer which satisfies the condition 2≤m≤4, and is preferably 2. Also, n is an integer which satisfies the condition 1≤n≤4, and is preferably 2.

Because the sulfonic acid ester compound of formula (1) exhibits a high solubility in a broad range of solvents, including low-polarity solvents, the physical properties of the solution can be adjusted using a variety of solvents, and the solution has a high coatability. Therefore, it is preferable for application to be carried out while the solution is in the state of a sulfonic acid ester, and for sulfonic acid to be generated when the applied film is dried or baked. Because it is desirable for the sulfonic acid ester to be stable at room temperature and at or below the baking temperature, the temperature at which sulfonic acid is generated from the sulfonic acid ester is typically from 40 to 260° C. Taking into account the high stability of the sulfonic acid ester within the varnish and the ease of dissociation during baking, the temperature is preferably from 80 to 230° C., and more preferably from 120 to 180° C.

The sulfonic acid ester compound of formula (1) can be rendered into a charge-transporting varnish by dissolution or dispersion, together with the charge-transporting substance serving as the central part of the charge transport mechanism, in an organic solvent.

The sulfonic acid ester compound of formula (1) can be synthesized by, for example, as shown in Reaction Scheme A below, reacting a sulfonic acid salt compound of formula (1″) with a halogenating agent so as to synthesize a sulfonyl halide compound of formula (1′) below (referred to below as "Step 1"), and then reacting this sulfonyl halide compound with a glycol ether of formula (2) (referred to below as "Step 2").

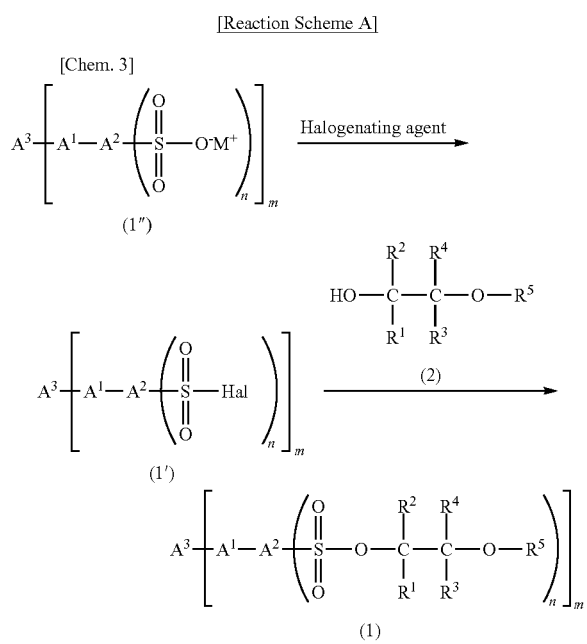

Here, $A^1$ to $A^3$, $R^1$ to $R^5$, m and n are as defined above; $M^+$ is a monovalent cation such as a sodium ion, potassium ion, pyridinium ion or quaternary ammonium ion; and Hal is a halogen atom such as a chlorine atom or bromine atom.

The sulfonic acid salt compound of formula (1″) can be synthesized by a known method.

Examples of the halogenating agent used in Step 1 include thionyl chloride, oxalyl chloride, phosphorus oxychloride and phosphorus(V) chloride; thionyl chloride is preferred. The amount of halogenating agent used is not limited, so long as it is at least one mole per mole of the sulfonic acid salt compound, although use in an amount that, expressed as a weight ratio, is from 2 to 10 times the amount of the sulfonic acid salt compound is preferred.

The reaction solvent used in Step 1 is preferably a solvent that does not react with the halogenating agent, examples of which include chloroform, dichloroethane, carbon tetrachloride, hexane and heptane, although the absence of a solvent is preferred. When the reaction is carried out in the absence of a solvent, the halogenating agent is preferably used in at least the amount at which the system becomes a uniform solution at the time of reaction completion. The reaction temperature may be set to from about 0° C. to about 150° C., although the reaction temperature is preferably from 20 to 100° C. and at or below the boiling point of the halogenating agent used. Following reaction completion, the crude product obtained by vacuum concentration or the like is generally used in the next step.

Preferred examples of the glycol ether of formula (2) include propylene glycol monoethyl ether, propylene glycol monopropyl ether, propylene glycol monobutyl ether, propylene glycol monophenyl ether, ethylene glycol monobutyl ether and ethylene glycol monohexyl ether.

In Step 2, a base may be concomitantly used. Examples of bases that may be used include sodium hydride, pyridine, triethylamine and diisopropylethylamine. Sodium hydride, pyridine and triethylamine are preferred. The base is preferably used in an amount that ranges from one mole per mole of the sulfonyl halide compound (1′) up to the amount of solvent.

Various organic solvents may be used as the reaction solvent in Step 2, although tetrahydrofuran, dichloroethane, chloroform and pyridine are preferred. The reaction temperature, although not particularly limited, is preferably from 0 to 80° C. Following reaction completion, pure sulfonic acid ester compound can be obtained by work-up and purification using customary methods such as vacuum concentration, liquid/liquid extraction, water rinsing, reprecipitation, recrystallization and chromatography. The pure sulfonic acid ester compound thus obtained can be rendered into a high-purity sulfonic acid compound by being subjected to heat treatment or the like.

Alternatively, as shown in Reaction Scheme B below, the sulfonic acid ester compound of formula (1) can be synthesized from a sulfonic acid compound of formula (1‴). In the reaction scheme shown below, the halogenating agent, glycol ether of formula (2), reaction solvent and other ingredients used in the first-stage and second-stage reactions may be the same as those used in Steps 1 and 2 of Reaction Scheme A.

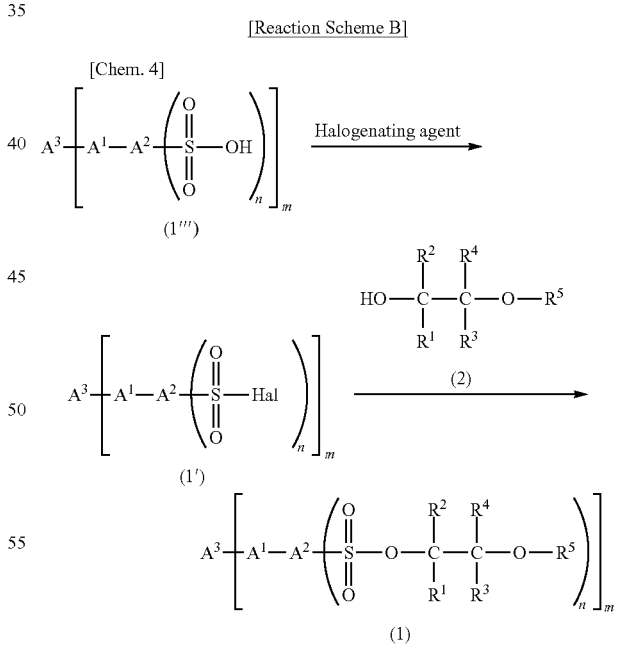

Here, $A^1$ to $A^3$, $R^1$ to $R^5$, m, n and Hal are as defined above.

The sulfonic acid compound of formula (1‴) may be synthesized according to, for example, the method described in WO 2006/025342.

[Charge-Transporting Varnish]

The charge-transporting varnish of the invention includes an electron-accepting substance precursor consisting of the compound of formula (1), a charge-transporting substance, and an organic solvent. In this invention, "charge-transportability" is synonymous with electrical conductivity. Also, "charge-transporting varnish" may refer to a varnish which itself has charge transportability or to one from which there can be obtained a solid film having charge transportability.

[Charge-Transporting Substance]

A charge-transporting substance hitherto used in the organic EL field may be used as the above charge-transporting substance. Examples include charge-transporting oligomers such as aniline derivatives, thiophene derivatives and pyrrole derivatives. The molecular weight of the charge-transporting oligomer is typically from 200 to 8,000. From the standpoint of preparing a varnish which gives thin films having a high charge transportability, the molecular weight is preferably at least 300, more preferably at least 400, and even more preferably at least 500. From the standpoint of preparing a uniform varnish that gives thin films having a high flatness, the molecular weight is preferably not more than 6,000, more preferably not more than 5,000, even more preferably not more than 4,000, and still more preferably not more than 3,000.

Of the above charge-transporting oligomers, taking into account the balance between the solubility in organic solvents and the charge transportability of the resulting thin film, aniline derivatives are preferred. Exemplary aniline derivatives include the oligoaniline derivatives mentioned in JP-A 2002-151272, the oligoaniline compounds mentioned in WO 2004/105446, the oligoaniline compounds mentioned in WO 2008/032617, the oligoaniline compounds mentioned in WO 2008/032616, the aryldiamine compounds mentioned in WO 2013/042623, and the aniline derivatives mentioned in WO 2015/050253 and WO 2016/190326.

The aniline derivative used may be, for example, a compound of formula (D1) or (D2).

[Chem. 5]

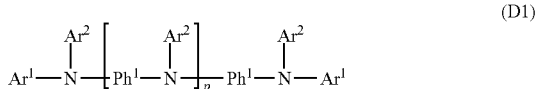

(D1)

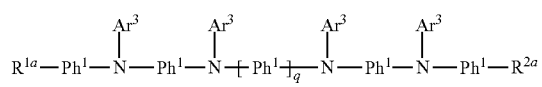

(D2)

In formula (D2), $R^{1a}$ and $R^{2a}$ are each independently a hydrogen atom, a halogen atom, a nitro group, a cyano group, or an alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom.

Examples of halogen atoms include fluorine, chlorine, bromine and iodine atoms.

The alkyl group of 1 to 20 carbon atoms may be linear, branched or cyclic. Specific examples include linear or branched alkyl groups of 1 to 20 carbon atoms such as methyl, ethyl, n-propyl, isopropyl, n-butyl, isobutyl, s-butyl, tert-butyl, n-pentyl, n-hexyl, n-heptyl, n-octyl, n-nonyl and n-decyl groups; and cyclic alkyl groups of 3 to 20 carbon atoms such as cyclopropyl, cyclobutyl, cyclopentyl, cyclohexyl, cycloheptyl, cyclooctyl, cyclononyl, cyclodecyl, bicyclobutyl, bicyclopentyl, bicyclohexyl, bicycloheptyl, bicyclooctyl, bicyclononyl and bicyclodecyl groups.

The alkenyl group of 2 to 20 carbon atoms may be linear, branched or cyclic. Specific examples include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl and n-1-eicosenyl groups.

The alkynyl group of 2 to 20 carbon atoms may be linear, branched or cyclic. Specific examples include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl and n-1-eicosynyl groups.

Specific examples of the aryl group of 6 to 20 carbon atoms include phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups.

Specific examples of the heteroaryl group of 2 to 20 carbon atoms include 2-thienyl, 3-thienyl, 2-furanyl, 3-furanyl, 2-oxazolyl, 4-oxazolyl, 5-oxazolyl, 3-isooxazolyl, 4-isooxazolyl, 5-isooxazolyl, 2-thiazolyl, 4-thiazolyl, 5-thiazolyl, 3-isothiazolyl, 4-isothiazolyl, 5-isothiazolyl, 2-imidazolyl, 4-imidazolyl, 2-pyridyl, 3-pyridyl and 4-pyridyl groups.

Of these, $R^{1a}$ and $R^{2a}$ are preferably hydrogen atoms, fluorine atoms, cyano groups, alkyl groups of 1 to 20 carbon atoms which may be substituted with halogen atoms, aryl groups of 6 to 20 carbon atoms which may be substituted with halogen atoms, or heteroaryl groups of 2 to 20 carbon atoms which may be substituted with halogen atoms; more preferably hydrogen atoms, fluorine atoms, cyano groups, alkyl groups of 1 to 10 carbon atoms which may be substituted with halogen atoms, or phenyl groups which may be substituted with halogen atoms; even more preferably hydrogen atoms or fluorine atoms; and most preferably hydrogen atoms.

$Ph^1$ in above formulas (D1) and (D2) represent groups of the formula (P1).

[Chem. 6]

(P1)

Here, $R^{3a}$ to $R^{6a}$ are each independently hydrogen atoms, halogen atoms, nitro groups, cyano groups, or alkyl groups of 1 to 20 carbon atoms, alkenyl groups of 2 to 20 carbon atoms, alkynyl groups of 2 to 20 carbon atoms, aryl groups of 6 to 20 carbon atoms or heteroaryl groups of 2 to 20 carbon atoms which may be substituted with a halogen atom. Specific examples of these are exemplified in the same way as described above for $R^{1a}$ and $R^{2a}$.

In particular, $R^{3a}$ to $R^{6a}$ are preferably hydrogen atoms, fluorine atoms, cyano groups, alkyl groups of 1 to 20 carbon atoms which may be substituted with halogen atoms, aryl groups of 6 to 20 carbon atoms which may be substituted with halogen atoms, or heteroaryl groups of 2 to 20 carbon atoms which may be substituted with halogen atoms; more preferably hydrogen atoms, fluorine atoms, cyano groups, alkyl groups of 1 to 10 carbon atoms which may be substituted with halogen atoms, or phenyl groups which may be substituted with halogen atoms; even more preferably hydrogen atoms or fluorine atoms; and most preferably hydrogen atoms.

Specific examples of groups suitable as $Ph^1$ include, but are not limited to, the following.

[Chem. 7]

(P1-1)

Each $Ar^1$ in formula (D1) above is independently a group of any of formulas (B1) to (B11), and more preferably a group of any of formulas (B1') to (B11').

[Chem. 8]

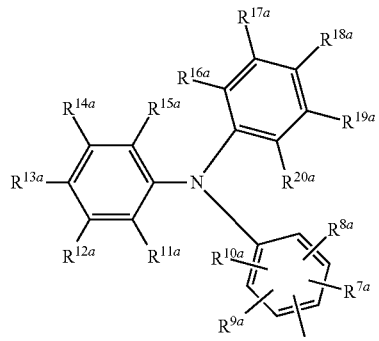

(B1)

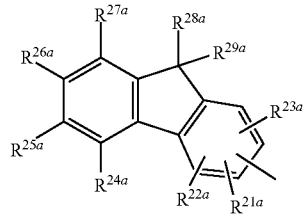

(B2)

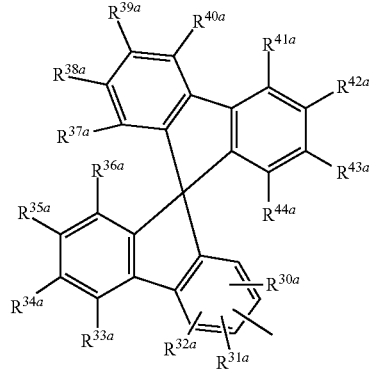

(B3)

-continued

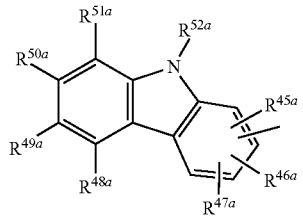

(B4)

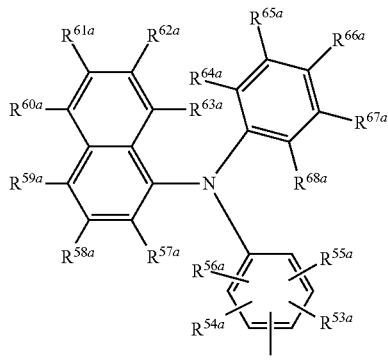

(B5)

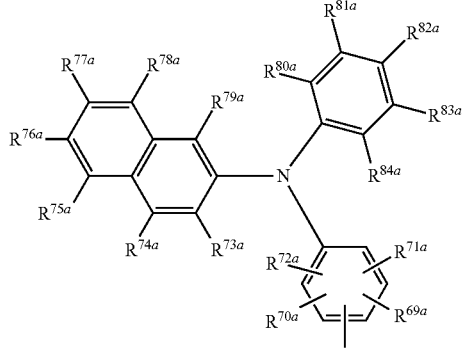

(B6)

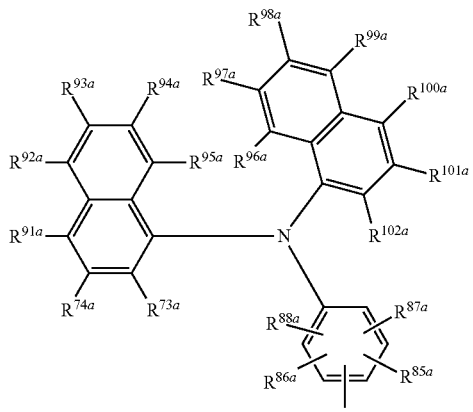

(B7)

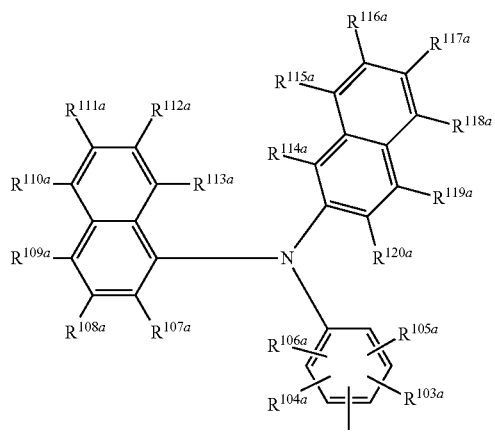
(B8)
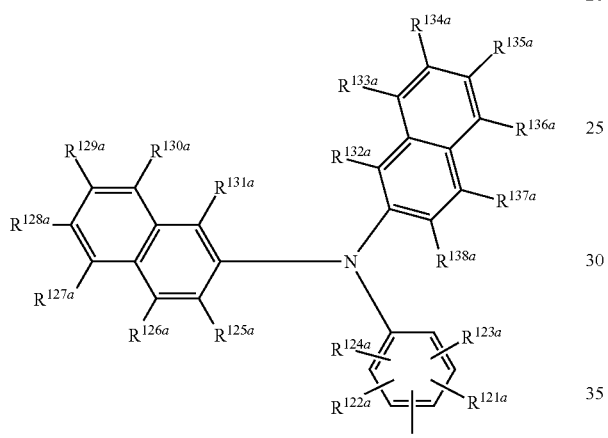
(B9)
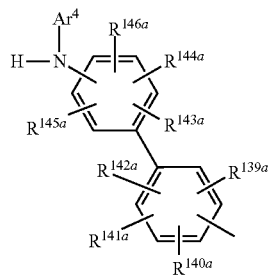
(B10)
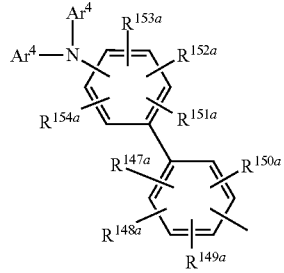
(B11)
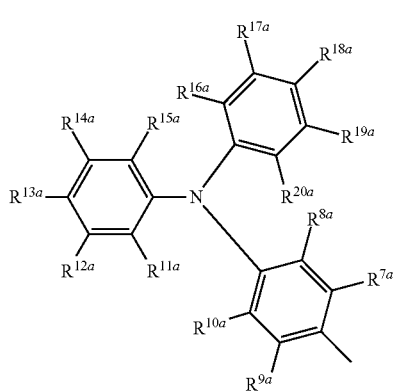
(B1′)
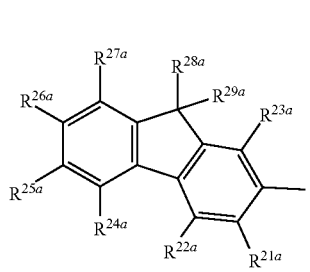
(B2′)
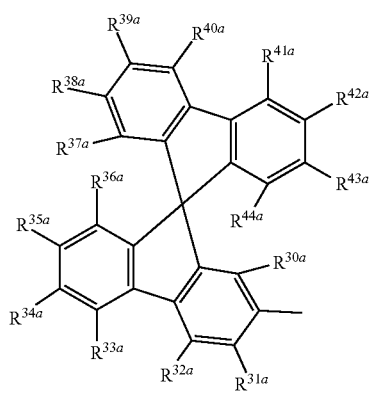
(B3′)
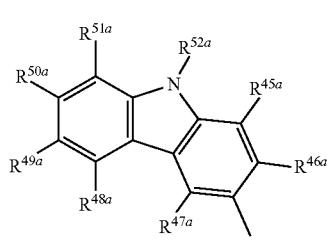
(B4′)

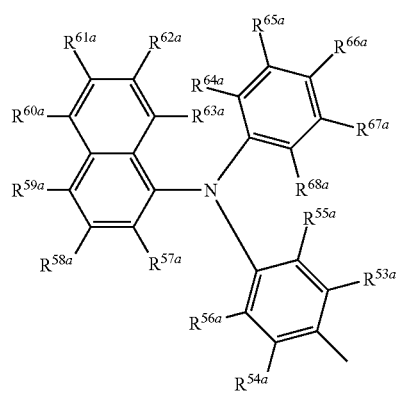
(B5')
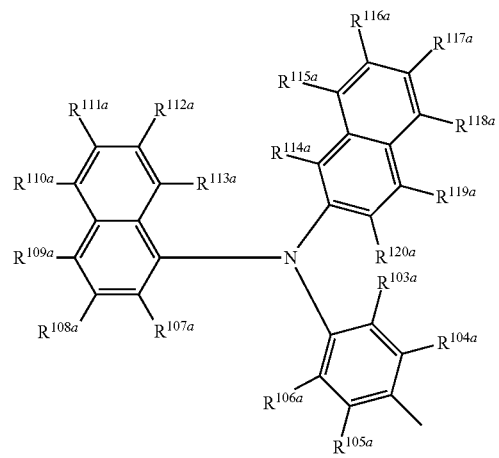
(B8')
(B9')
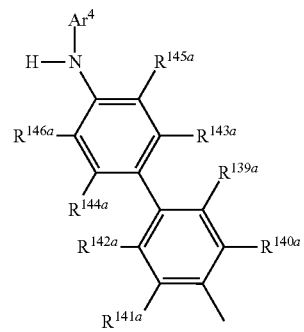
(B6')
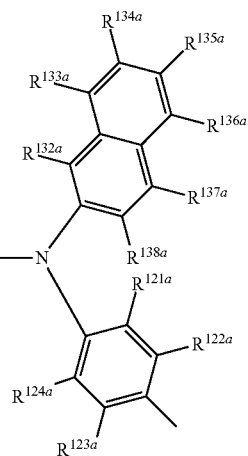
(B10')
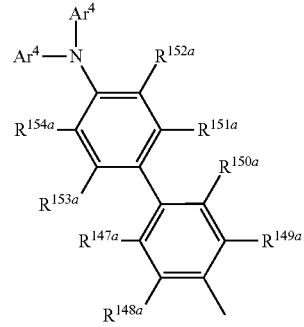
(B7')
(B11')

Each Ar² in formula (D1) above is independently a group of any of formulas (G1) to (G18).
[Chem. 10]
(G1)
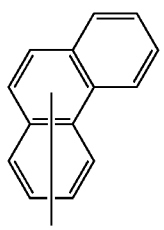
(G2)
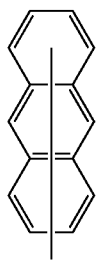
(G3)
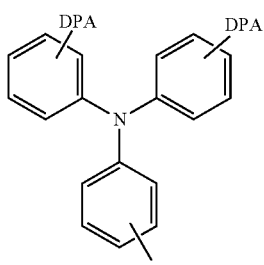
(G4)
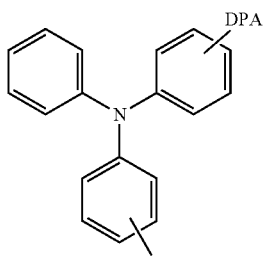
(G5)
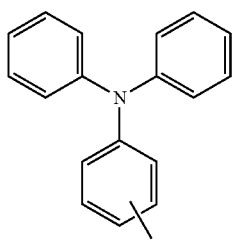
(G6)
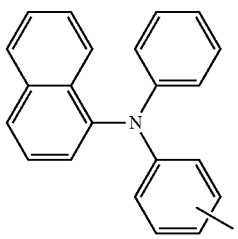
(G7)
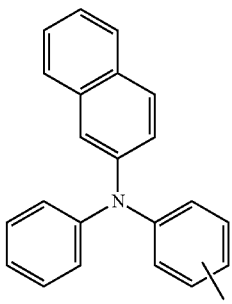
(G8)
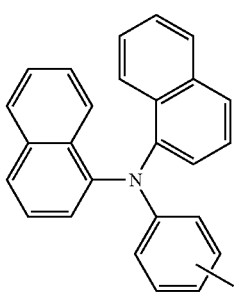
(G9)
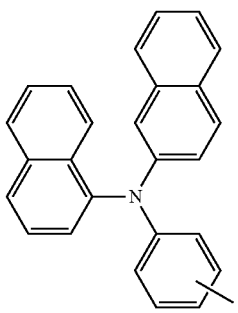
(G10)
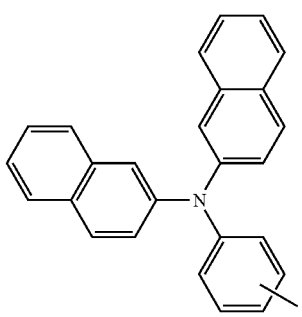
(G11)

(G12) 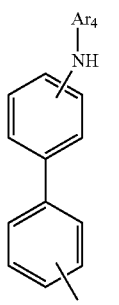

(G13) 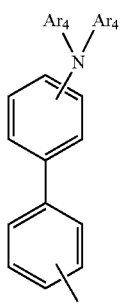

(G14) 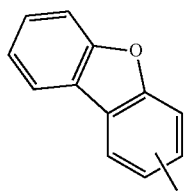

(G15) 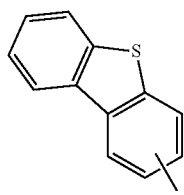

(G16) 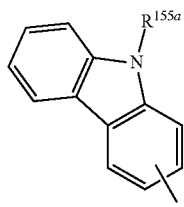

(G17) 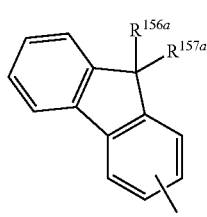

(G18) 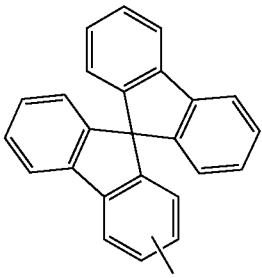

In these formulas, $R^{155a}$ is preferably a hydrogen atom, an aryl group of 6 to 14 carbon atoms which may be substituted with $Z^{1a}$, or a heteroaryl group of 2 to 14 carbon atoms which may be substituted with $Z^{1a}$; more preferably a hydrogen atom, a phenyl group which may be substituted with $Z^{1a}$, a 1-naphthyl group which may be substituted with $Z^{1a}$, a 2-naphthyl group which may be substituted with $Z^{1a}$, a 2-pyridyl group which may be substituted with $Z^{1a}$, a 3-pyridyl group which may be substituted with a phenyl group that may be substituted with $Z^{1a}$, or a 4-pyridyl group which may be substituted with $Z^1$; even more preferably a phenyl group which may be substituted with $Z^{1a}$; and most preferably a phenyl group or a (2,3,5,6-tetrafluoro-4-(trifluoromethyl)phenyl) group.

$R^{156a}$ and $R^{157a}$ are preferably aryl groups of 6 to 14 carbon atoms which may be substituted with a phenyl group that may be substituted with $Z^{1a}$ or heteroaryl groups of 2 to 14 carbon atoms that may be substituted with a phenyl group that may be substituted with $Z^{1a}$; more preferably aryl groups of 6 to 14 carbon atoms which may be substituted with a phenyl group that may be substituted with $Z^{1a}$; and even more preferably phenyl groups which may be substituted with a phenyl group that may be substituted with $Z^{1a}$, 1-naphthyl groups which may be substituted with a phenyl group that may be substituted with $Z^{1a}$ or 2-naphthyl groups which may be substituted with $Z^1$.

$Ar^3$ in above formula (D2) is a group represented by any of formulas (I1) to (I8). A group represented by any of formulas (I1') to (I8') is especially preferred.

[Chem. 11]

(I1)

(I2)

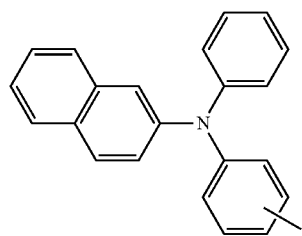 (I3)
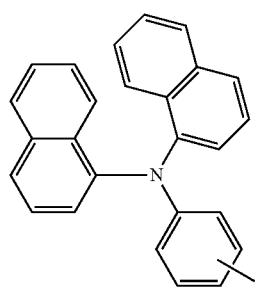 (I4)
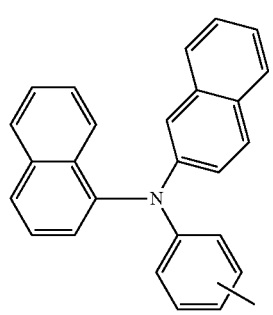 (I5)
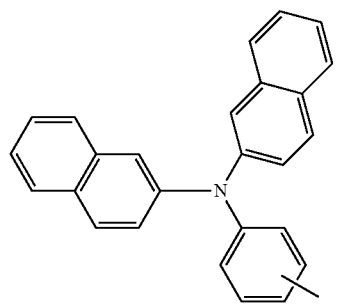 (I6)
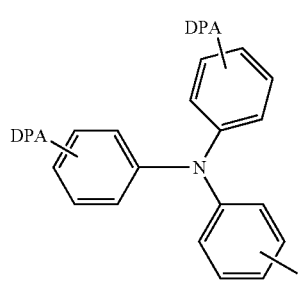 (I7)
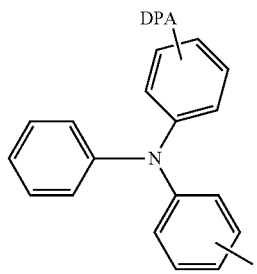 (I8)
[Chem. 12]
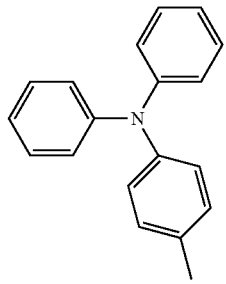 (I1′)
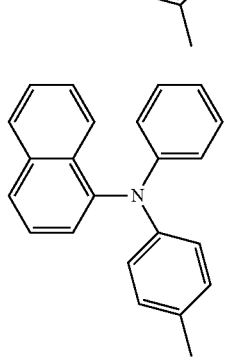 (I2′)
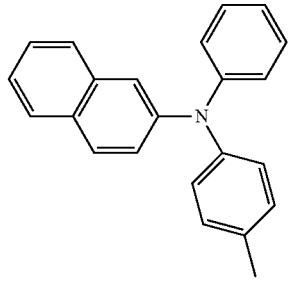 (I3′)
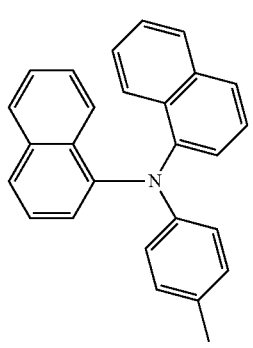 (I4′)

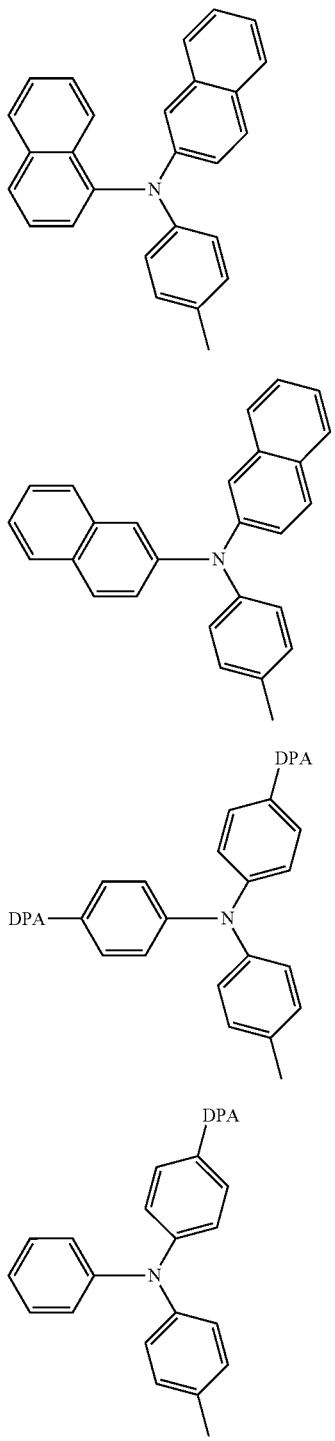

Here, $R^{7a}$ to $R^{27a}$, $R^{30a}$ to $R^{51a}$ and $R^{53a}$ to $R^{154a}$ are each independently a hydrogen atom, a halogen atom, a nitro group, a cyano group, or a diphenylamino group, alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms that may be substituted with a halogen atom; $R^{28a}$ and $R^{29a}$ are each independently an aryl group of 6 to 20 carbon atoms or heteroaryl group of 2 to 20 carbon atoms which may be substituted with $Z^{1a}$; $R^{52a}$ is a hydrogen atom, or an aryl group of 6 to 20 carbon atoms or heteroaryl group of 2 to 20 carbon atoms which may be substituted with $Z^{1a}$; $Z^{1a}$ is a halogen atom, a nitro group, a cyano group, or an alkyl group of 1 to 20 carbon atoms, alkenyl group of 2 to 20 carbon atoms or alkynyl group of 2 to 20 carbon atoms which may be substituted with $Z^{2a}$; $Z^{2a}$ is a halogen atom, a nitro group, a cyano group, or an aryl group of 6 to 20 carbon atoms or heteroaryl group of 2 to 20 carbon atoms which may be substituted with $Z^{3a}$; and $Z^{3a}$ is a halogen atom, a nitro group or a cyano group. These halogen atoms, alkyl groups of 1 to 20 carbon atoms, alkenyl groups of 2 to 20 carbon atoms, alkynyl groups of 2 to 20 carbon atoms, aryl groups of 6 to 20 carbon atoms and heteroaryl groups of 2 to 20 carbon atoms are exemplified in the same way as described above for $R^{1a}$ and $R^{2a}$.

In particular, $R^{7a}$ to $R^{27a}$, $R^{30a}$ to $R^{51a}$ and $R^{53a}$ to $R^{145a}$ are preferably hydrogen atoms, fluorine atoms, cyano groups, diphenylamino groups which may be substituted with halogen atoms, alkyl groups of 1 to 20 carbon atoms which may be substituted with halogen atoms, aryl groups of 6 to 20 carbon atoms which may be substituted with halogen atoms or heteroaryl groups of 2 to 20 carbon atoms which may be substituted with halogen atoms; more preferably hydrogen atoms, fluorine atoms, cyano groups, alkyl groups of 1 to 10 carbon atoms which may be substituted with halogen atoms or phenyl groups which may be substituted with halogen atoms; even more preferably hydrogen atoms or fluorine atoms; and most preferably hydrogen atoms.

Also, $R^{28a}$ and $R^{29a}$ are preferably aryl groups of 6 to 20 carbon atoms which may be substituted with halogen atoms or heteroaryl groups of 2 to 20 carbon atoms which may be substituted with halogen atoms; more preferably phenyl groups which may be substituted with halogen atoms or naphthyl groups which may be substituted with halogen atoms; even more preferably phenyl groups which may be substituted with halogen atoms; and still more preferably phenyl groups.

$R^{52a}$ is preferably a hydrogen atom or an aryl group of 6 to 20 carbon atoms which may be substituted with $Z^{1a}$; more preferably a hydrogen atom, a phenyl group which may be substituted with $Z^{1a}$, or a naphthyl group which may be substituted with $Z^{1a}$; even more preferably a phenyl group which may be substituted with $Z^{1a}$; and still more preferably a phenyl group.

Each $Ar^4$ is independently an aryl group of 6 to 20 carbon atoms which may be substituted with a di($C_{6-20}$ aryl)amino group.

Specific examples of the aryl group of 6 to 20 carbon atoms include the same as those mentioned above for $R^{1a}$ and $R^{2a}$. Specific examples of the di($C_{6-20}$ aryl)amino group include diphenylamino, 1-naphthylphenylamino, di(1-naphthyl)amino, 1-naphthyl-2-naphthylamino and di(2-naphthyl)amino groups.

$Ar^4$ is preferably a phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, p-(diphenylamino)phenyl, p-(1-naphthylphenylamino)phenyl, p-(di(1-naphthyl)amino)phenyl, p-(1-naphthyl-2-naphthylamino)phenyl or p-(di(2-naphthyl)amino)phenyl group; and more preferably a p-(diphenylamino)phenyl group.

The subscript p in formula (D1) is an integer from 1 to 10. From the standpoint of increasing the solubility in organic solvents, p is preferably from 1 to 5, more preferably from 1 to 3, even more preferably 1 or 2, and most preferably 1.

The subscript q in formula (D2) is 1 or 2.

In addition, aniline derivatives that may be used are exemplified by fluorine atom-containing oligoaniline derivatives of formula (D3) below.

[Chem. 13]

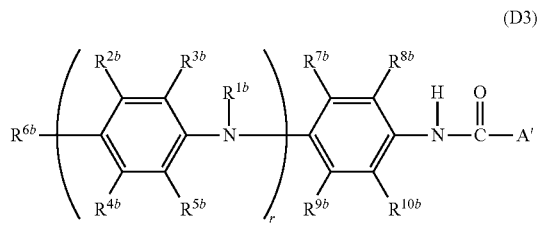

(D3)

In the formula, $R^{1b}$ is a hydrogen atom or an alkyl group of 1 to 20 carbon atoms which may be substituted with $Z^b$. $Z^b$ represents a halogen atom, a nitro group, a cyano group, an aldehyde group, a hydroxyl group, a thiol group, a sulfonic acid group, a carboxyl group, an aryl group of 6 to 20 carbon atoms which may be substituted with $Z^{b'}$ or a heteroaryl group of 2 to 20 carbon atoms which may be substituted with $Z^{b'}$. $Z^{b'}$ represents a halogen atom, a nitro group, a cyano group, an aldehyde group, a hydroxyl group, a thiol group, a sulfonic acid group or a carboxyl group.

$R^{2b}$ to $R^{10b}$ are each independently a hydrogen atom, a halogen atom, a nitro group, a cyano group, or an alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with halogen atoms.

Specific examples of the halogen atoms, alkyl groups of 1 to 20 carbon atoms, alkenyl groups of 2 to 20 carbon atoms, alkynyl groups of 2 to 20 carbon atoms, aryl groups of 6 to 20 carbon atoms and heteroaryl groups of 2 to 20 carbon atoms include the same as those mentioned above.

Of these, taking into account the solubility of the oligoaniline derivative in organic solvents, $R^{1b}$ is preferably a hydrogen atom or an alkyl group of 1 to 10 carbon atoms which may be substituted with $Z^b$; more preferably a hydrogen atom or an alkyl group of 1 to 4 carbon atoms which may be substituted with $Z^b$; and most preferably a hydrogen atom. In cases where there are a plurality of $R^{1b}$ moieties, they may each be the same or may be different.

In cases where $R^{1b}$ is a hydrogen atom, a particularly outstanding charge transportability can be achieved when the oligoaniline derivative is used together with a dopant such as a protic acid (e.g., an arylsulfonic acid or a heteropolyacid).

Of these, taking into account the solubility of the oligoaniline derivative in organic solvents, $R^{2b}$ to $R^{10b}$ are preferably hydrogen atoms, halogen atoms, nitro groups, cyano groups or alkyl groups of 1 to 10 carbon atoms which may be substituted with halogen atoms; and more preferably hydrogen atoms, halogen atoms or alkyl groups of 1 to 4 carbon atoms which may be substituted with halogen atoms. Taking into account the balance between the solubility of the oligoaniline derivative in organic solvents and the charge transportability, $R^{2b}$ to $R^{10b}$ are most preferably hydrogen atoms. In cases where there are a plurality of $R^{2b}$ to $R^{5b}$ moieties, they may each be the same or may be different.

In formula (D3), A' is a fluoroalkyl group of 1 to 20 carbon atoms, fluorocycloalkyl group of 3 to 20 carbon atoms, fluorobicycloalkyl group of 4 to 20 carbon atoms, fluoroalkenyl group of 2 to 20 carbon atoms or fluoroalkynyl group of 2 to 20 carbon atoms which may be substituted with a cyano group, chlorine atom, bromine atom, iodine atom, nitro group or fluoroalkoxy group of 1 to 20 carbon atoms; a fluoroaryl group of 6 to 20 carbon atoms which may be substituted with a cyano group, chlorine atom, bromine atom, iodine atom, nitro group, alkyl group of 1 to 20 carbon atoms, fluoroalkyl group of 1 to 20 carbon atoms or fluoroalkoxy group of 1 to 20 carbon atoms; an aryl group of 6 to 20 carbon atoms which is substituted with a fluoroalkyl group of 1 to 20 carbon atoms, fluorocycloalkyl group of 3 to 20 carbon atoms, fluorobicycloalkyl group of 4 to 20 carbon atoms, fluoroalkenyl group of 2 to 20 carbon atoms or fluoroalkynyl group of 2 to 20 carbon atoms and may also be substituted with a cyano group, halogen atom or fluoroalkoxy group of 1 to 20 carbon atoms; a fluoroaralkyl group of 7 to 20 carbon atoms which may be substituted with a cyano group, chlorine atom, bromine atom, iodine atom, nitro group, fluoroalkoxy group of 1 to 20 carbon atoms, fluoroalkyl group of 1 to 20 carbon atoms, fluorocycloalkyl group of 3 to 20 carbon atoms, fluorobicycloalkyl group of 4 to 20 carbon atoms, fluoroalkenyl group of 2 to 20 carbon atoms or fluoroalkynyl group of 2 to 20 carbon atoms; or an aralkyl group of 7 to 20 carbon atoms which is substituted with a fluoroalkyl group of 1 to 20 carbon atoms, fluorocycloalkyl group of 3 to 20 carbon atoms, fluorobicycloalkyl group of 4 to 20 carbon atoms, fluoroalkenyl group of 2 to 20 carbon atoms or fluoroalkynyl group of 2 to 20 carbon atoms and may also be substituted with a cyano group, a halogen atom or a fluoroalkoxy group of 1 to 20 carbon atoms.

The fluoroalkyl group is not particularly limited, provided that it is a linear or branched alkyl group in which at least one hydrogen atom on a carbon atom is substituted with a fluorine atom. Examples include fluoromethyl, difluoromethyl, trifluoromethyl, 1-fluoroethyl, 2-fluoroethyl, 1,2-difluoroethyl, 1,1-difluoroethyl, 2,2-difluoroethyl, 1,1,2-trifluoroethyl, 1,2,2-trifluoroethyl, 2,2,2-trifluoroethyl, 1,1,2,2-tetrafluoroethyl, 1,2,2,2-tetrafluoroethyl, 1,1,2,2,2-pentafluoroethyl, 1-fluoropropyl, 2-fluoropropyl, 3-fluoropropyl, 1,1-difluoropropyl, 1,2-difluoropropyl, 1,3-difluoropropyl, 2,2-difluoropropyl, 2,3-difluoropropyl, 3,3-difluoropropyl, 1,1,2-trifluoropropyl, 1,1,3-trifluoropropyl, 1,2,3-trifluoropropyl, 1,3,3-trifluoropropyl, 2,2,3-trifluoropropyl, 2,3,3-trifluoropropyl, 3,3,3-trifluoropropyl, 1,1,2,2-tetrafluoropropyl, 1,1,2,3-tetrafluoropropyl, 1,2,2,3-tetrafluoropropyl, 1,3,3,3-tetrafluoropropyl, 2,2,3,3-tetrafluoropropyl, 2,3,3,3-tetrafluoropropyl, 1,1,2,2,3-pentafluoropropyl, 1,2,2,3,3-pentafluoropropyl, 1,1,3,3,3-pentafluoropropyl, 1,2,3,3,3-pentafluoropropyl, 2,2,3,3,3-pentafluoropropyl and heptafluoropropyl groups.

The fluorocycloalkyl group is not particularly limited, provided that it is a cycloalkyl group in which at least one hydrogen atom on a carbon atom is substituted with a fluorine atom. Examples include 1-fluorocyclopropyl, 2-fluorocyclopropyl, 2,2-difluorocyclopropyl, 2,2,3,3-tetrafluorocyclopropyl, pentafluorocyclopropyl, 2,2-difluorocyclobutyl, 2,2,3,3-tetrafluorocyclobutyl, 2,2,3,3,4,4-hexafluorocyclobutyl, heptafluorocyclobutyl, 1-fluorocyclopentyl, 3-fluorocyclopentyl, 3,3-difluorocyclopentyl, 3,3,4,4-tetrafluorocyclopentyl, nonafluorocyclopentyl, 1-fluorocyclohexyl, 2-fluorocyclohexyl, 4-fluorocyclohexyl, 4,4-difluorocyclohexyl, 2,2,3,3-tetrafluorocyclohexyl, 2,3,4,5,6-pentafluorocyclohexyl and undecafluorocyclohexyl groups.

The fluorobicycloalkyl group is not particularly limited, provided that it is a bicycloalkyl group in which at least one hydrogen atom on a carbon atom is substituted with a fluorine atom. Examples include 3-fluorobicyclo[1.1.0]butan-1-yl, 2,2,4,4-tetrafluorobicyclo[1.1.0]butan-1-yl, pentafluorobicyclo[1.1.0]butan-1-yl, 3-fluorobicyclo[1.1.1]pentan-1-yl, 2,2,4,4,5-pentafluorobicyclo[1.1.1]pentan-1-yl, 2,2,4,4,5,5-hexafluorobicyclo[1.1.1]pentan-1-yl, 5-fluorobicyclo[3.1.0]hexan-6-yl, 6-fluorobicyclo[3.1.0]hexan-6-yl, 6,6-difluorobicyclo[3.1.0]hexan-2-yl, 2,2,3,3,5,5,6,6-octafluorobicyclo[2.2.0]hexan-1-yl, 1-fluorobicyclo[2.2.1]heptan-2-yl, 3-fluorobicyclo[2.2.1]heptan-2-yl, 4-fluorobicyclo[2.2.1]heptan-1-yl, 5-fluorobicyclo[3.1.1]heptan-1-yl, 1,3,3,4,5,5,6,6,7,7-decafluorobicyclo[2.2.1]heptan-2-yl, undecafluorobicyclo[2.2.1]heptan-2-yl, 3-fluorobicyclo[2.2.2]octan-1-yl and 4-fluorobicyclo[2.2.2]octan-1-yl groups.

The fluoroalkenyl group is not particularly limited, provided that it is an alkenyl group in which at least one hydrogen atom on a carbon atom is substituted with a fluorine atom. Examples include 1-fluoroethenyl, 2-fluoroethenyl, 1,2-difluoroethenyl, 1,2,2-trifluoroethenyl, 2,3,3-trifluoro-1-propenyl, 3,3,3-trifluoro-1-propenyl, 2,3,3,3-tetrafluoro-1-propenyl, pentafluoro-1-propenyl, 1-fluoro-2-propenyl, 1,1-difluoro-2-propenyl, 2,3-difluoro-2-propenyl, 3,3-difluoro-2-propenyl, 2,3,3-trifluoro-2-propenyl, 1,2,3,3-tetrafluoro-2-propenyl and pentafluoro-2-propenyl groups.

The fluoroalkynyl group is not particularly limited, provided that it is an alkynyl group in which at least one hydrogen atom on a carbon atom is substituted with a fluorine atom. Examples include fluoroethynyl, 3-fluoro-1-propynyl, 3,3-difluoro-1-propynyl, 3,3,3-trifluoro-1-propynyl, 1-fluoro-2-propynyl and 1,1-difluoro-2-propynyl groups.

The fluoroaryl group is not particularly limited, provided that it is an aryl group in which at least one hydrogen atom on a carbon atom is substituted with a fluorine atom. Examples include 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 3,4,5-trifluorophenyl, 2,3,4,5-tetrafluorophenyl, 2,3,4,6-tetrafluorophenyl, 2,3,5,6-tetrafluorophenyl, pentafluorophenyl, 2-fluoro-1-naphthyl, 3-fluoro-1-naphthyl, 4-fluoro-1-naphthyl, 6-fluoro-1-naphthyl, 7-fluoro-1-naphthyl, 8-fluoro-1-naphthyl, 4,5-difluoro-1-naphthyl, 5,7-difluoro-1-naphthyl, 5,8-difluoro-1-naphthyl, 5,6,7,8-tetrafluoro-1-naphthyl, heptafluoro-1-naphthyl, 1-fluoro-2-naphthyl, 5-fluoro-2-naphthyl, 6-fluoro-2-naphthyl, 7-fluoro-2-naphthyl, 5,7-difluoro-2-naphthyl and heptafluoro-2-naphthyl groups.

The fluoroaryl group, taking into account the balance between, for example, the solubility of the oligoaniline derivative in organic solvents, the charge transportability of the oligoaniline derivative and the availability of starting materials for the oligoaniline derivative, is preferably a phenyl group which is substituted with three or more fluorine atoms and which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms.

The fluoroalkoxy group is not particularly limited, provided that it is an alkoxy group in which at least one hydrogen atom on a carbon atom is substituted with a fluorine atom. Examples include fluoromethoxy, difluoromethoxy, trifluoromethoxy, 1-fluoroethoxy, 2-fluoroethoxy, 1,2-difluoroethoxy, 1,1-difluoroethoxy, 2,2-difluoroethoxy, 1,1,2-trifluoroethoxy, 1,2,2-trifluoroethoxy, 2,2,2-trifluoroethoxy, 1,1,2,2-tetrafluoroethoxy, 1,2,2,2-tetrafluoroethoxy, 1,1,2,2,2-pentafluoroethoxy, 1-fluoropropoxy, 2-fluoropropoxy, 3-fluoropropoxy, 1,1-difluoropropoxy, 1,2-difluoropropoxy, 1,3-difluoropropoxy, 2,2-difluoropropoxy, 2,3-difluoropropoxy, 3,3-difluoropropoxy, 1,1,2-trifluoropropoxy, 1,1,3-trifluoropropoxy, 1,2,3-trifluoropropoxy, 1,3,3-trifluoropropoxy, 2,2,3-trifluoropropoxy, 2,3,3-trifluoropropoxy, 3,3,3-trifluoropropoxy, 1,1,2,2-tetrafluoropropoxy, 1,1,2,3-tetrafluoropropoxy, 1,2,2,3-tetrafluoropropoxy, 1,3,3,3-tetrafluoropropoxy, 2,2,3,3-tetrafluoropropoxy, 2,3,3,3-tetrafluoropropoxy, 1,1,2,2,3-pentafluoropropoxy, 1,2,2,3,3-pentafluoropropoxy, 1,1,3,3,3-pentafluoropropoxy, 1,2,3,3,3-pentafluoropropoxy, 2,2,3,3,3-pentafluoropropoxy and heptafluoropropoxy groups.

The aryl group of 6 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms and may also be substituted with a cyano group, a halogen atom or a fluoroalkoxy group of 1 to 20 carbon atoms (which aryl group is also referred to below, for the sake of convenience, as a "substituted aryl group") is not particularly limited, provided that it is an aryl group in which at least one hydrogen atom on a carbon atom is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms. Examples include 2-(trifluoromethyl)phenyl, 3-(trifluoromethyl)phenyl, 4-(trifluoromethyl)phenyl, 4-ethoxy-3-(trifluoromethyl)phenyl, 3-fluoro-4-(trifluoromethyl)phenyl, 4-fluoro-3-(trifluoromethyl)phenyl, 4-fluoro-2-(trifluoromethyl)phenyl, 2-fluoro-5-(trifluoromethyl)phenyl, 3-fluoro-5-(trifluoromethyl)phenyl, 3,5-di(trifluoromethyl)phenyl, 2,4,6-tri(trifluoromethyl)phenyl, 4-(pentafluoroethyl)phenyl, 4-(3,3,3-trifluoropropyl)phenyl, 2,3,5,6-tetrafluoro-4-(trifluoromethyl)phenyl, 4-(perfluorovinyl)phenyl, 4-(perfluoropropenyl)phenyl and 4-(perfluorobutenyl)phenyl groups.

The substituted aryl group, taking into account the balance between the solubility of the oligoaniline derivative in organic solvents, the charge transportability of the oligoaniline derivative and the availability of starting materials for the oligoaniline derivative, is preferably a phenyl group which is substituted with a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms and which may also be substituted with a cyano group, a halogen atom or a fluoroalkoxy group of 1 to 20 carbon atoms (which phenyl group is also referred to below, for the sake of convenience, as a "substituted phenyl group"); more preferably a phenyl group substituted with from one to three trifluoromethyl groups; and even more preferably a p-trifluoromethylphenyl group.

The fluoroaralkyl group is not particularly limited, provided it is an aralkyl group in which at least one hydrogen atom on a carbon atom is substituted with a fluorine atom. Examples include 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2,3,4-trifluorobenzyl, 2,3,5-trifluorobenzyl, 2,3,6-trifluorobenzyl, 2,4,5-trifluorobenzyl, 2,4,6-trifluorobenzyl, 2,3,4,5-tetrafluorobenzyl, 2,3,4,6-tetrafluorobenzyl, 2,3,5,6-tetraflurobenzyl and 2,3,4,5,6-pentafluorobenzyl groups.

The aralkyl group of 7 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms and may be substituted with a cyano group, a halogen atom or a fluoroalkoxy group of 1 to 20 carbon atoms is not particularly limited, provided it is an aralkyl group in which at least one hydrogen atom on a carbon atom is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms. Examples include 2-trifluoromethylbenzyl, 3-trifluoromethylbenzyl, 4-trifluoromethylbenzyl, 2,4-di(trifluoromethyl)benzyl, 2,5-di(trifluoromethyl)benzyl, 2,6-di(trifluoromethyl)benzyl, 3,5-di(trifluoromethyl)benzyl and 2,4,6-tri(trifluoromethyl)benzyl groups.

Of these, A' is preferably the above fluoroalkyl group of 1 to 20 carbon atoms which may be substituted, the above fluoroaryl group of 6 to 20 carbon atoms which may be substituted or the above substituted aryl group; more preferably the above fluoroaryl group of 6 to 20 carbon atoms which may be substituted or the above substituted aryl group; even more preferably the above fluorophenyl group which may be substituted or the above substituted phenyl group; and still more preferably the above trifluorophenyl group which may be substituted, the above tetrafluorophenyl group which may be substituted, the above pentafluorophenyl group which may be substituted or a phenyl group substituted with from one to three trifluoromethyl groups.

Also, the subscript r is an integer from 1 to 20. However, from the standpoint of the solubility of the oligoaniline derivative in solvents, r is preferably 10 or less, more preferably 8 or less, even more preferably 5 or less, and still more preferably 4 or less. From the standpoint of increasing the charge transportability of the oligoaniline derivative, the subscript r is preferably 2 or more, and more preferably 3 or more. Taking into account the balance between solubility and charge transportability, the subscript r is most preferably 3.

Preferred use can be made of the aniline derivatives of formula (3) below.

Specific examples of alkyl groups of 1 to 20 carbon atoms, alkenyl groups of 2 to 20 carbon atoms, alkynyl groups of 2 to 20 carbon atoms, aryl groups of 6 to 20 carbon atoms and heteroaryl groups of 2 to 20 carbon atoms include the same as those mentioned above.

$R^{107}$ and $R^{108}$ are each independently a hydrogen atom, a chlorine atom, a bromine atom, an iodine atom, a nitro group, a cyano group, an amino group, an aldehyde group, a hydroxyl group, a thiol group, a sulfonic acid group, a carboxyl group, an alkyl group of 1 to 20 carbon atoms, alkenyl group of 2 to 20 carbon atoms or alkynyl group of 2 to 20 carbon atoms which may be substituted with $Z^1$, an aryl group of 6 to 20 carbon atoms or heteroaryl group of 2 to 20 carbon atoms which may be substituted with $Z^2$, or —$NHY^2$, —$NY^3Y^4$, —$C(O)Y^5$, —$OY^6$, —$SY^7$, —$SO_3Y^8$, —$C(O)OY^9$, —$OC(O)Y^{10}$, —$C(O)NHY^{11}$ or —$C(O)NY^{12}Y^{13}$.

$Y^2$ to $Y^{13}$ are each independently an alkyl group of 1 to 20 carbon atoms, alkenyl group of 2 to 20 carbon atoms or alkynyl group of 2 to 20 carbon atoms which may be substituted with $Z^1$, or an aryl group of 6 to 20 carbon atoms or heteroaryl group of 2 to 20 carbon atoms which may be substituted with $Z^2$.

$Z^1$ is a chlorine atom, a bromine atom, an iodine atom, a nitro group, a cyano group, an amino group, an aldehyde group, a hydroxyl group, a thiol group, a sulfonic acid group, a carboxyl group, or an aryl group of 6 to 20 carbon atoms or heteroaryl group of 2 to 20 carbon atoms which may be substituted with Z.

$Z^2$ is a chlorine atom, a bromine atom, an iodine atom, a nitro group, a cyano group, an amino group, an aldehyde group, a hydroxyl group, a thiol group, a sulfonic acid group, a carboxyl group, or an alkyl group of 1 to 20 carbon atoms, alkenyl group of 2 to 20 carbon atoms or alkynyl group of 2 to 20 carbon atoms which may be substituted with $Z^3$.

$Z^3$ is a chlorine atom, a bromine atom, an iodine atom, a nitro group, a cyano group, an amino group, an aldehyde group, a hydroxyl group, a thiol group, a sulfonic acid group or a carboxyl group.

The alkyl, alkenyl, alkynyl, aryl and heteroaryl groups on $R^{107}$, $R^{108}$ and $Y^2$ to $Y^{13}$ are exemplified in the same way as described above.

Of these, $R^{107}$ and $R^{108}$ are preferably hydrogen atoms or alkyl groups of 1 to 20 carbon atoms which may be

[Chem. 14]

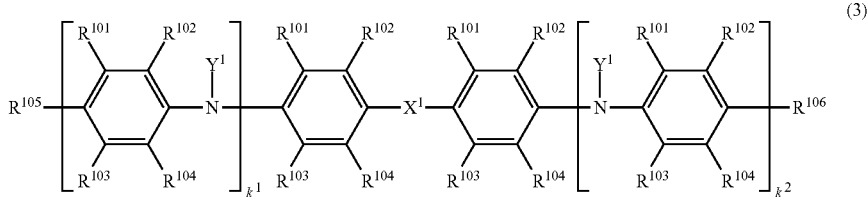

(3)

In formula (3), $X^1$ represents —$NY^1$—, —O—, —S—, —$(CR^{107}R^{108})_L$— or a single bond. When $k^1$ or $k^2$ is 0, $X^1$ represents —$NY^1$—.

Each $Y^1$ is independently a hydrogen atom, an alkyl group of 1 to 20 carbon atoms, alkenyl group of 2 to 20 carbon atoms or alkynyl group of 2 to 20 carbon atoms which may be substituted with $Z^1$, or an aryl group of 6 to 20 carbon atoms or heteroaryl group of 2 to 20 carbon atoms which may be substituted with $Z^2$.

substituted with $Z^1$, more preferably hydrogen atoms or methyl groups which may be substituted with $Z^1$, and most preferably both hydrogen atoms.

L, which represents the number of divalent groups of the formula —$(CR^{107}R^{108})$—, is an integer from 1 to 20, preferably from 1 to 10, more preferably from 1 to 5, even more preferably 1 or 2, and most preferably 1. When L is 2 or more, the plurality of $R^{107}$ groups may be mutually the same or different, and the plurality of $R^{108}$ may be mutually the same or different.

In particular, $X^1$ is preferably —$NY^1$— or a single bond. $Y^1$ is preferably a hydrogen atom or an alkyl group of 1 to 20 carbon atoms which may be substituted with $Z^1$, more preferably a hydrogen atom or a methyl group which may be substituted with $Z^1$, and most preferably a hydrogen atom.

In formula (3), $R^{101}$ to $R^{106}$ are each independently a hydrogen atom, a chlorine atom, a bromine atom, an iodine atom, a nitro group, a cyano group, an amino group, an aldehyde group, a hydroxyl group, a thiol group, a sulfonic acid group, a carboxyl group, an alkyl group of 1 to 20 carbon atoms, alkenyl group of 2 to 20 carbon atoms or alkynyl group of 2 to 20 carbon atoms which may be substituted with $Z^1$, an aryl group of 6 to 20 carbon atoms or heteroaryl group of 2 to 20 carbon atoms which may be substituted with $Z^2$, or —$NHY^2$, —$NY^3Y^4$, —$C(O)Y^5$, —$OY^6$, —$SY^7$, —$SO_3Y^8$, —$C(O)OY^9$, —$OC(O)Y^{10}$, —$C(O)NHY^{11}$ or —$C(O)NY^{12}Y^{13}$ (wherein $Y^2$ to $Y^{13}$ are as defined above). These alkyl, alkenyl, alkynyl, aryl and heteroaryl groups are exemplified in the same way as above.

In particular, in formula (3), $R^{101}$ to $R^{104}$ are each preferably a hydrogen atom, a halogen atom, an alkyl group of 1 to 10 carbon atoms which may be substituted with $Z^1$, or an aryl group of 6 to 14 carbon atoms which may be substituted with $Z^2$; more preferably a hydrogen atom or an alkyl group of 1 to 10 carbon atoms; and most preferably are all hydrogen atoms.

$R^{105}$ and $R^{106}$ are each preferably a hydrogen atom, a chlorine atom, a bromine atom, an iodine atom, an alkyl group of 1 to 10 carbon atoms which may be substituted with $Z^1$, an aryl group of 6 to 14 carbon atoms which may be substituted with $Z^2$, or a diphenylamino group which may be substituted with $Z^2$ (the phenyl group —$NY^3Y^4$ wherein $Y^3$ and $Y^4$ may be substituted with $Z^2$); are more preferably a hydrogen atom or a diphenylamino group; and are even more preferably both hydrogen atoms or both diphenylamino groups.

Of these, a combination in which $R^{101}$ to $R^{104}$ are each preferably a hydrogen atom or an alkyl group of 1 to 10 carbon atoms, $R^{105}$ and $R^{106}$ are each a hydrogen atom or a diphenylamino group, $X^1$ is —$NY^1$— or a single bond and $Y^1$ is a hydrogen atom or a methyl group is preferred; and a combination in which $R^{101}$ to $R^{104}$ are each a hydrogen atom, $R^{105}$ and $R^{106}$ are both hydrogen atoms or diphenylamino groups, and $X^1$ is —NH— or a single bond is more preferred.

In formula (3), $k^1$ and $k^2$ are each independently an integer of 0 or more and together satisfy the condition $1 \leq k^1 + k^2 \leq 20$. Taking into account the balance between the charge transportability of the resulting thin film and the solubility of the aniline derivative, they preferably satisfy the condition $2 \leq k^1 + k^2 \leq 8$, more preferably satisfy the condition $2 \leq k^1 + k^2 \leq 6$, and even more preferably satisfy the condition $2 \leq k^1 + k^2 \leq 4$.

In $Y^1$ to $Y^{13}$ and $R^{101}$ to $R^{108}$, $Z^1$ is preferably a chlorine atom, a bromine atom, an iodine atom or an aryl group of 6 to 20 carbon atoms which may be substituted with $Z^3$; more preferably a chlorine atom, a bromine atom, an iodine atom or a phenyl group which may be substituted with $Z^3$; and most preferably does not exist (i.e., is non-substituting).

$Z^2$ is preferably a chlorine atom, a bromine atom, an iodine atom or an alkyl group of 1 to 20 carbon atoms which may be substituted with $Z^3$, more preferably a chlorine atom, a bromine atom, an iodine atom or an alkyl group of 1 to 4 carbon atoms which may be substituted with $Z^3$; and most preferably does not exist (i.e., is non-substituting).

$Z^3$ is preferably a chlorine atom, a bromine atom or an iodine atom; and most preferably does not exist (i.e., is non-substituting).

In $Y^1$ to $Y^{13}$ and $R^{101}$ to $R^{108}$, the number of carbon atoms on the alkyl, alkenyl and alkynyl groups is preferably 10 or less, more preferably 6 or less, and even more preferably 4 or less. The number of carbon atoms on the aryl and heteroaryl groups is preferably 14 or less, more preferably 10 or less, and even more preferably 6 or less.

The method of synthesizing the aniline derivative is exemplified by, without particular limitation, the methods described in *Bulletin of Chemical Society of Japan*, 67, pp. 1749-1752 (1994); *Synthetic Metals*, 84, pp. 119-120 (1997); *Thin Solid Films*, 520(24), pp. 7157-7163 (2012); and WO 2008/032617, WO 2008/032616, WO 2008/129947 and WO 2013/084664.

Specific examples of the aniline derivative of formula (3) include, but are not limited to, those of the following formulas. In the formulas below, "DPA" stands for a diphenylamino group, "Ph" stands for a phenyl group, and "TPA" stands for a p-(diphenylamino)phenyl group.

[Chem. 15]

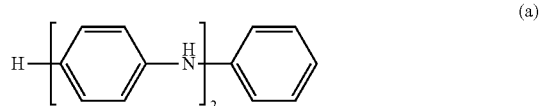
(a)

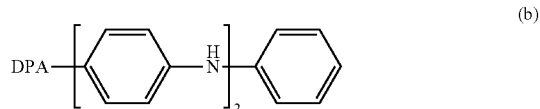
(b)

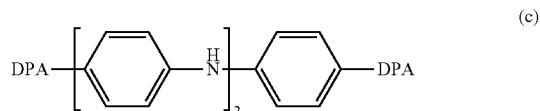
(c)

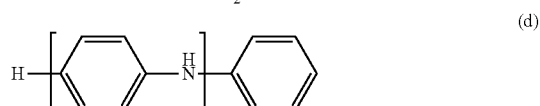
(d)

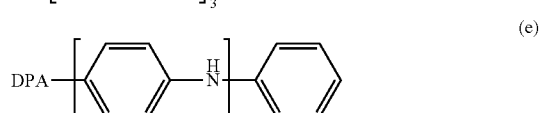
(e)

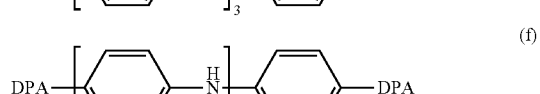
(f)

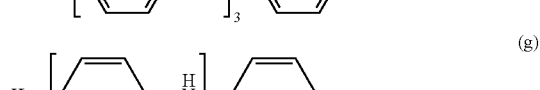
(g)

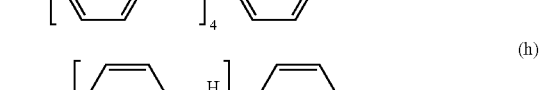
(h)

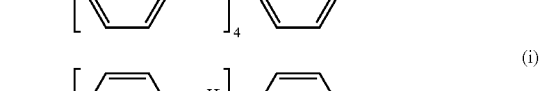
(i)

[Chem. 16]

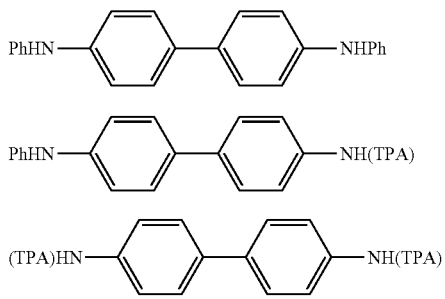

[Organic Solvent]

A high-solvency solvent capable of dissolving well the above aniline derivatives and sulfonic acid ester compounds may be used as the organic solvent employed when preparing the charge-transporting varnish of the invention. To dissolve an unesterified sulfonic acid compound, it is necessary that at least one highly polar solvent be included. By contrast, it is possible to dissolve the above sulfonic acid ester compounds in a solvent regardless of the polarity of the solvent. In this invention, a low-polarity solvent is defined as a solvent having a dielectric constant at a frequency of 100 kHz that is less than 7, and a high-polarity solvent is defined as a solvent having a dielectric constant at a frequency of 100 kHz that is 7 or more.

Examples of low-polarity solvents include
chlorinated solvents such as chloroform and chlorobenzene;
aromatic hydrocarbon solvents such as toluene, xylene, tetralin, cyclohexylbenzene and decylbenzene;
aliphatic alcohol solvents such as 1-octanol, 1-nonanol and 1-decanol;
ether solvents such as tetrahydrofuran, dioxane, anisole, 4-methoxytoluene, 3-phenoxytoluene, dibenzyl ether, diethylene glycol dimethyl ether, diethylene glycol butyl methyl ether, triethylene glycol dimethyl ether and triethylene glycol butyl methyl ether, and ester solvents such as methyl benzoate, ethyl benzoate, butyl benzoate, isoamyl benzoate, bis(2-ethylhexyl) phthalate, dibutyl maleate, dibutyl oxalate, hexyl acetate, diethylene glycol monoethyl ether acetate and diethylene glycol monobutyl ether acetate.

Examples of high-polarity solvents include
amide solvents such as N,N-dimethylformamide, N,N-dimethylacetamide, N,N-dimethylisobutyramide, N-methylpyrrolidone and 1,3-dimethyl-2-imidazolidinone;
ketone solvents such as ethyl methyl ketone, isophorone and cyclohexanone;
cyano solvents such as acetonitrile and 3-methoxypropionitrile;
polyhydric alcohol solvents such as ethylene glycol, diethylene glycol, triethylene glycol, dipropylene glycol, 1,3-butanediol and 2,3-butanediol;
monohydric alcohol solvents other than aliphatic alcohols, such as diethylene glycol monomethyl ether, diethylene glycol monophenyl ether, triethylene glycol monomethyl ether, dipropylene glycol monomethyl ether, benzyl alcohol, 2-phenoxyethanol, 2-benzyloxyethanol, 3-phenoxybenzyl alcohol and tetrahydrofurfuryl alcohol; and sulfoxide solvents such as dimethylsulfoxide.
Depending on the intended use, these solvents may be used singly or two or more may be used in admixture.

It is preferable for all the charge-transporting substances to be in a completely dissolved or uniformly dispersed state in the above solvent, and more preferable for them to be completely dissolved.

In this invention, from the standpoint of reproducibly obtaining thin films having a higher flatness, it is desirable for the charge-transporting varnish to be obtained by dissolving the charge-transporting substance in the organic solvent and subsequently filtering the solution using a sub-micron-order filter or the like.

The solids concentration in the varnish of the invention, from the standpoint of ensuring a sufficient film thickness while minimizing deposition of the charge-transporting substance, is generally from about 0.1 wt % to about 20 wt %, and preferably from 0.5 to 10 wt %. As used herein, "solids" refers to the constituents that remain when the solvent is removed from the ingredients included in the varnish. The viscosity of the inventive varnish is generally from 1 to 50 mPa·s at 25° C.

The content of the electron-accepting substance precursor within these solids, expressed as a molar ratio with respect to unity (1) for the charge-transporting substance, is preferably from about 0.01 to about 20, and more preferably from about 0.05 to about 15.

[Charge-Transporting Thin Film]

A charge-transporting thin film can be formed on a substrate by applying the charge-transporting varnish of the invention onto the substrate and drying the applied varnish.

Examples of methods for applying the varnish include, but are not limited to, dipping, spin coating, transfer printing, roll coating, brush coating, inkjet coating, spraying and slit coating. It is preferable for the viscosity and surface tension of the varnish to be adjusted according to the method of application.

When using the varnish of the invention, the liquid film drying conditions are not particularly limited; one example is heating and baking on a hot plate. A dry film can be obtained by heating and baking in a temperature range of generally from about 100° C. to about 260° C. for a period of from about 1 minute to about 1 hour. The baking atmosphere also is not particularly limited.

The thickness of the charge-transporting thin film is not particularly limited. However, when the thin film is to be used as a functional layer in an organic EL device, a film thickness of from 5 to 200 nm is preferred. Methods for changing the film thickness include, for example, changing the solids concentration in the varnish and changing the amount of solution on the substrate at the time of application.

[Organic EL Device]

The organic EL device of the invention has a pair of electrodes and additionally has, between these electrodes, the above-described charge-transporting thin film of the invention.

Typical organic EL device configurations include, but are not limited to, configurations (a) to (f) below. In these configurations, where necessary, an electron-blocking layer or the like may be provided between the light-emitting layer and the anode, and a hole-blocking layer or the like may be provided between the light-emitting layer and the cathode. Alternatively, the hole-injecting layer, hole-transporting layer or hole-injecting-and-transporting layer may also have the function of an electron-blocking layer or the like; and the electron-injecting layer, electron-transporting layer or electron-injecting-and-transporting layer may also have the function of a hole-blocking layer or the like.

(a) anode/hole-injecting layer/hole-transporting layer/light-emitting layer/electron-transporting layer/electron-injecting layer/cathode
(b) anode/hole-injecting layer/hole-transporting layer/light-emitting layer/electron-injecting-and-transporting layer/cathode
(c) anode/hole-injecting-and-transporting layer/light-emitting layer/electron-transporting layer/electron-injecting layer/cathode
(d) anode/hole-injecting-and-transporting layer/light-emitting layer/electron-injecting-and-transporting layer/cathode
(e) anode/hole-injecting layer/hole-transporting layer/light-emitting layer/cathode
(f) anode/hole-injecting-and-transporting layer/light-emitting layer/cathode As used herein, "hole-injecting layer," "hole-transporting layer" and "hole-injecting-and-transporting layer" refer to layers which are formed between the light-emitting layer and the anode and which have the function of transporting holes from the anode to the light-emitting layer. When only one layer of hole-transporting material is provided between the light-emitting layer and the anode, this is a "hole-injecting-and-transporting layer"; when two or more layers of hole-transporting material are provided between the light-emitting layer and the anode, the layer that is closer to the anode is a "hole-injecting layer" and the other layer is a "hole-transporting layer." In particular, thin films having not only an excellent ability to accept holes from the anode but also an excellent ability to inject holes into, respectively, the hole-transporting layer and the light-emitting layer may be used as the hole-injecting layer and the hole-injecting-and-transporting layer.

In addition, "electron-injecting layer," "electron-transporting layer" and "electron-injecting-and-transporting layer" refer to layers which are formed between the light-emitting layer and the cathode and which have the function of transporting electrons from the cathode to the light-emitting layer. When only one layer of electron-transporting material is provided between the light-emitting layer and the cathode, this is an "electron-injecting-and-transporting layer"; when two or more layers of electron-transporting material are provided between the light-emitting layer and the cathode, the layer that is closer to the cathode is an "electron-injecting layer" and the other layer is an "electron-transporting layer."

The "light-emitting layer" is an organic layer having a light-emitting function. When a doping system is used, this layer includes a host material and a dopant material. The function of the host material is primarily to promote the recombination of electrons and holes and to confine the resulting excitons within the light-emitting layer. The function of the dopant material is to cause the excitons obtained by recombination to efficiently luminesce. In the case of phosphorescent devices, the host material functions primarily to confine within the light-emitting layer the excitons generated by the dopant.

The materials and method employed to produce an organic EL device using the charge-transporting varnish of the invention are exemplified by, but not limited to, those described below.

The electrode substrate to be used is preferably cleaned beforehand by liquid washing with, for example, a cleaning agent, alcohol or pure water. For example, when the electrode substrate is an anode substrate, it is preferably subjected to surface treatment such as UV/ozone treatment or oxygen-plasma treatment just prior to use. However, surface treatment need not be carried out in cases where the anode material is composed primarily of organic substances.

An example is described below of a method for producing the organic EL device of the invention in which a thin-film obtained from the charge-transporting varnish of the invention serves as the hole-injecting layer.

Using the above-described method, a hole-injecting layer is formed on an electrode by applying the charge-transporting varnish of the invention onto an anode substrate and then baking the applied varnish. A hole-transporting layer, a light-emitting layer, an electron-transporting layer, an electron-injecting layer and a cathode are provided in this order on the hole-injecting layer. The hole-transporting layer, light-emitting layer, electron-transporting layer and electron-injecting layer may be formed by either a vapor deposition process or a coating process (wet process), depending on the properties of the material used.

Illustrative examples of anode materials include transparent electrodes such as indium-tin oxide (ITO) and indium-zinc oxide (IZO), and metal anodes made of a metal such as aluminum or an alloy of such a metal. An anode material on which planarizing treatment has been carried out is preferred. Use can also be made of polythiophene derivatives and polyaniline derivatives having a high charge transportability.

Examples of other metals that may make up the metal anode include, but are not limited to, scandium, titanium, vanadium, chromium, manganese, iron, cobalt, nickel, copper, zinc, gallium, yttrium, zirconium, niobium, molybdenum, ruthenium, rhodium, palladium, cadmium, indium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof.

Specific examples of hole-transporting layer-forming materials include the following hole-transporting low-molecular-weight materials: triarylamines such as
(triphenylamine) dimer derivatives, [(triphenylamine) dimer] spirodimer,
N,N'-bis(naphthalen-1-yl)-N,N'-bis(phenyl)benzidine (α-NPD),
N,N'-bis(naphthalen-2-yl)-N,N'-bis(phenyl)benzidine,
N,N'-bis(3-methylphenyl)-N,N'-bis(phenyl)benzidine,
N,N'-bis(3-methylphenyl)-N,N'-bis(phenyl)-9,9-spirobifluorene,
N,N'-bis(naphthalen-1-yl)-N,N'-bis(phenyl)-9,9-spirobifluorene,
N,N'-bis(3-methylphenyl)-N,N'-bis(phenyl)-9,9-dimethylfluorene,
N,N'-bis(naphthalen-1-yl)-N,N'-bis(phenyl)-9,9-dimethylfluorene,
N,N'-bis(3-methylphenyl)-N,N'-bis(phenyl)-9,9-diphenylfluorene,
N,N'-bis(naphthalen-1-yl)-N,N'-bis(phenyl)-9,9-diphenylfluorene,
N,N'-bis(naphthalen-1-yl)-N,N'-bis(phenyl)-2,2'-dimethylbenzidine,
2,2',7,7'-tetrakis(N,N-diphenylamino)-9,9-spirobifluorene,
9,9-bis[4-(NN-bis-biphenyl-4-ylamino)phenyl]-9H-fluorene,
9,9-bis[4-(N,N-bisnaphthalen-2-ylamino)phenyl]-9H-fluorene,
9,9-bis[4-(N-naphthalen-1-yl-N-phenylamino)phenyl]-9H-fluorene,
2,2',7,7'-tetrakis[N-naphtalenyl(phenyl)amino]-9,9-spirobifluorene, N,N'-bis(phenanthren-9-yl)-N,N'-bis(heny)benzidine,
2,2'-bis[N,N-bis(biphenyl-4-yl)amino]-9,9-spirobifluorene,
2,2'-bis(N,N-diphenyl amino)-9,9-spirobifluorene,
di[4-(N,N-di(p-tolyl)amino)phenyl]cyclohexane,
2,2',7,7'-tetra(NN-di(p-tolyl))amino-9,9-spirobifluorene,
N,N N',N'-tetra-naphthalen-2-yl-benzidine,
N,N,N',N'-tetra(3-methylphenyl)-3,3'-dimethylbenzidine,
N,N'-di(naphthalenyl)-N,N'-di(naphthalen-2-yl)benzidine,
N,N,N',N'-tetra(naphthalenyl)benzidine,
N,N'-di(naphthalen-2-yl)-N,N'-diphenylbenzidine-1-4-diamine,
$N^1,N^4$-diphenyl-$N^1,N^4$-di(m-tolyl)benzene-1,4-diamine,
$N^2,N^2,N^6,N^6$-tetraphenylnaphthalene-2,6-diamine, tris(4-(quinolin-8-yl)phenyl)amine,
2,2'-bis(3-(N,N-di(p-tolyl)amino)phenyl)biphenyl,
4,4',4''-tris[3-methylphenyl(phenyl)amino]triphenylamine (m-MTDATA) and
4,4',4''-tris[1-naphthyl(phenyl)amino]triphenylamine (1-TNATA); and oligothiophenes such as
5,5''-bis-{4-[bis(4-methylphenyl)amino]phenyl}-2,2':5',2''-terthiophene (BMA-3T).

Specific examples of light-emitting layer-forming materials include
tris(S-quinolinolate) aluminum(III) (Alq₃), bis(8-quinolinolate) zinc(II) (Znq2),
bis(2-methyl-8-quinolinolate)-4-(p-phenylphenolate) aluminum(III) (BAlq),
4,4'-bis(2,2-diphenylvinyl)biphenyl, 9,10-di(naphthalen-2-yl)anthracene,
2-tert-butyl-9,10-di(naphthalen-2-yl)anthracene,
2,7-bis[9,9-di(4-methylphenyl)-fluoren-2-yl]-9,9-di(4-methylphenyl)fluorene,
2-methyl-9,10-bis(naphthalen-2-yl)anthracene,
2-(9,9-spirobifluoren-2-yl)-9,9-spirobifluorene,
2,7-bis(9,9-spirobifluoren-2-yl)-9,9-spirobifluorene,
2-[9,9-di(4-methylphenyl)-fluoren-2-yl]-9,9-di(4-methylphenyl)fluorene,
2,2'-dipyrenyl-9,9-spirobifluorene, 1,3,5-tris(pyren-1-yl)benzene,
9,9-bis[4-(pyrenyl)phenyl]-9H-fluorene, 2,2'-bi(9,10-diphenylanthracene),
2,7-dipyrenyl-9,9-spirobifluorene, 1,4-di(pyren-1-yl)benzene, 1,3-di(pyren-1-yl)benzene,
6,13-di(biphenyl-4-yl)pentacene, 3,9-di(naphthalen-2-yl)perylene,
3,10-di(naphthalen-2-yl)perylene, tris[4-(pyrenyl)-phenyl] amine,
10,10'-di(biphenyl-4-yl)-9,9'-bianthracene,
N,N'-di(naphthalen-1-yl)-N,N'-diphenyl-[1,1':4',1'':4'',1'''-quaterphenyl]-4,4'''-diamine,
4,4'-di[10-(naphthalen-1-yl)anthracen-9-yl]biphenyl,
dibenzo{[f,f]-4,4',7,7'-tetraphenyl}diindeno[1,2,3-cd: 1',2',3'-1m]perylene,
1-(7-(9,9'-bianthracen-10-yl)-9,9-dimethyl-9H-fluoren-2-yl)pyrene,
1-(7-(9,9'-bianthracen-10-yl)-9,9-dihexyl-9H-fluoren-2-yl) pyrene,
1,3-bis(carbazol-9-yl)benzene, 1,3,5-tris(carbazol-9-yl)benzene,
4,4',4''-tris(carbazol-9-yl)triphenylamine, 4,4'-bis(carbazol-9-yl)biphenyl (CBP),
4,4'-bis(carbazol-9-yl)-2,2'-dimethylbiphenyl, 2,7-bis(carbazol-9-yl)-9,9-dimethylfluorene,
2,2',7,7'-tetrakis(carbazol-9-yl)-9,9-spirobifluorene,
2,7-bis(carbazol-9-yl)-9,9-di(p-tolyl)fluorene, 9,9-bis[4-(carbazol-9-yl)-phenyl]fluorene,
2,7-bis(carbazol-9-yl)-9,9-spirobifluorene, 1,4-bis(triphenylsilyl)benzene,
1,3-bis(triphenylsilyl)benzene,
bis(4-N,N-diethylamino-2-methylphenyl)-4-methylphenylmethane,
2,7-bis(carbazol-9-yl)-9,9-dioctylfluorene, 4,4''-di(triphenylsilyl)-p-terphenyl,
4,4'-di(triphenylsilyl)biphenyl, 9-(4-tert-butylphenyl)-3,6-bis(triphenylsilyl)-9H-carbazole,
9-(4-tert-butylphenyl)-3,6-ditrityl-9H-carbazole,
9-(4-tert-butylphenyl)-3,6-bis(9(4-methoxyphenyl)-9H-fluoren-9-yl)-9H-carbazole,
2,6-bis(3-(9H-carbazol-9-yl)phenyl)pyridine,
triphenyl(4-(9-phenyl-9H-fluoren-9-yl)phenyl)silane,
9,9-dimethyl-N,N-diphenyl-7-(4-(1-phenyl-1H-benzo[d]imidazol-2-yl)phenyl-9H-fluoren-2-amine,
3,5-bis(3-(9H-carbazol-9-yl)phenyl)pyridine,
9,9-spirobifluoren-2-yl-diphenyl-phosphine oxide,
9,9'-(5-triphenylsilyl)-1,3-phenylene)bis(9H-carbazole),
3-(2,7-bi(diphenylphosphoryl)-9-phenyl-9H-fluoren-9-yl)-9-phenyl-9H-carbazole,
4,4,8,8,12,12-hexa(p-tolyl)-4H-8H-12H-12C-azadibenzo[cd,mn]pyrene,
4,7-di(9H-carbazol-9-yl)-1,10-phenanthroline, 2,2'-bis(4-(carbazol-9-yl)phenyl)biphenyl,
2,8-bis(diphenylphosphoryl)dibenzo[b,d]thiophene, bis(2-methylphenyl)diphenylsilane,
bis[3,5-di(9H-carbazol-9-yl)phenyl]diphenylsilane,
3,6-bis(carbazol-9-yl)-9-(2-ethylhexyl)-9H-carbazole,
3-(diphenylphosphoryl)-9-(4-(diphenylphosphoryl)phenyl)-9H-carbazole and
3,6-bis[(3,5-diphenyl)phenyl]-9-phenylcarbazole.

The light-emitting layer may be formed by the co-vapor deposition of these materials with a light-emitting dopant. Specific examples of light-emitting dopants include
3-(2-benzthiazolyl)-7-(diethylamino)coumarin,
2,3,6,7-tetrahydro-1,1,7,7-tetramethyl-1H,5H,11H-10-(2-benzothiazolyl)quinolidino-[9,9a,1gh]coumarin,
quinacridone, N,N'-dimethylquinacridone,
tris(2-phenylpyridine) iridium(III) (Ir(ppy)₃),
bis(2-phenylpyridine)(acetylacetonate) iridium(III) (Ir(ppy)₂(acac)),
tris[2-(p-tolyl)pyridine] iridium(III) (Ir(mppy)₃),
9,10-bis[N,N-di(p-tolyl)amino]anthracene,
9,10-bis[phenyl(m-tolyl)amino]anthracene,
bis[2-(2-hydroxyphenyl)benzothiazolate] zinc(II),
$N^{10},N^{10},N^{10'},N^{10'}$-tetra(p-tolyl)-9,9'-bianthracene-1,10'-diamine,
$N^{10},N^{10},N^{10'},N^{10'}$-tetraphenyl-9,9'-bianthracene-10,10'-diamine,
$N^{10},N^{10'}$-diphenyl-$N^{10},N^{10'}$-dinaphthalenyl-9,9'-bianthracene-10,10'-diamine,
4,4'-bis(9-ethyl-3-carbazovinylene)-1,1'-biphenyl,
perylene, 2,5,8,11-tetra-tert-butylperylene,
1,4-bis[2-(3-N-ethylcarbazolyl)vinyl]benzene,
4,4'-bis[4-(di-p-tolylamino)styryl]biphenyl,
4-(di-p-tolylamino)-4'-[(di-p-tolylamino)styryl]stilbene,
bis[3,5-difluoro-2-(2-pyridyl)phenyl-(2-carboxypyridyl)] iridium(III),
4,4'-bis[4-(diphenylamino)styryl]biphenyl,
bis(2,4-difluorophenylpyridinato)tetrakis(1-pyrazolyl)borate iridium(III),
N,N'-bis(naphthalen-2-yl)-N,N'-bis(phenyl)-tris(9,9-dimethylfluorenylene),
2,7-bis {2-[phenyl(m-tolyl)amino]-9,9-dimethylfluoren-7-yl}-9,9-dimethylfluorene, N-(4-((E)-2-(6((E)-4-(diphenylamino)styryl)naphthalen-2-yl)vinyl)phenyl)-N-phenylbenzenamine,
fac-iridium(III) tris(1-phenyl-3-methylbenzimidazolin-2-ylidene-C,$C^2$),
mer-iridium(III) tris(1-phenyl-3-methylbenzimidazolin-2-yliden-C,$C^2$),
2,7-bis[4-(diphenylamino)styryl]-9,9-spirobifluorene,
6-methyl-2-(4-(9-(4-(6-methylbenzo[d]thiazol-2-yl)phenyl)anthracen-10-yl)phenyl)benzo-[d]thiazole,
1,4-di[4-(N,N-diphenyl)amino]styrylbenzene,
1,4-bis(4 9H-carbazol-9-yl)styryl)benzene,
(E)-6-(4-(diphenylamino)styryl)-N,N-diphenylnaphthalen-2-amine,
bis(2,4-difluorophenylpyridinato)(5-(pyridin-2-yl)-1H-tetrazolate) iridium(III),
bis(3-trifluoromethyl-5-(2-pyridyl)pyrazole)((2,4-difluorobenzyl)diphenylphosphinate) iridium(III),
bis(3-trifluoromethyl-5-(2-pyridyl)pyrazolate)((benzyldiphenylphosphinate) iridium(III),
bis(1-(2,4-difluorobenzyl)-3-methylbenzimidazolium)(3-(trifluoromethyl)-5-(2-pyridyl)-1,2,4-triazolate) iridium (III),
bis(3-trifluoromethyl-5-(2-pyridyl)pyrazolate)(4',6'-difluorophenylpyridinate) iridium(III),
bis(4',6'-difluorophenylpyridinato)(3,5-bis(trifluoromethyl)-2-(2'-pyridyl)pyrrolate) iridium(III),
bis(4',6'-difluorophenylpyridinato)(3-(trifluoromethyl)-5-(2-pyridyl)-1,2,4-triazolate) iridium (III),
(Z)-6-mesityl-N-(6-mesitylquinolin-2(1H)-ylidene)quinoline-2-amine-$BF_2$,
(E)-2-(2-(4-(dimethylamino)styryl)-6-methyl-4H-pyran-4-ylidene)malononitrile,
4-(dicyanomethylene)-2-methyl-6-julolidyl-9-enyl-4H-pyran,
4-(dicyanomethylene)-2-methyl-6-(1,1,7,7-tetramethyljulolidyl-9-enyl)-4H-pyran,
4-(dicyanomethylene)-2-tert-butyl-6-(1,1,7,7-tetramethyljulolidin-4-ylvinyl)-4H-pyran, tris(dibenzoylmethane) phenanthroline europium(III),
5,6,11,12-tetraphenylnaphthacene,
bis(2-benzo[b]thiophen-2-yl-pyridine)(acetylacetonate) iridium(III),
tris(1-phenylisoquinoline) iridium(III),
bis(1-phenylisoquinoline)(acetylacetonate) iridium(III),
bis[1-(9,9-dimethyl-9H-fluoren-2-yl)isoquinoline](acetylacetonate) iridium(III),
bis[2-(9,9-dimethyl-9H-fluoren-2-yl)quinoline](acetylacetonate) iridium(III),
tris[4,4'-di-tert-butyl-(2,2')-bipyridine] ruthenium(III)-bis(hexafluorophosphate),
tris(2-phenylquinoline) iridium(III), bis(2-phenylquinoline)(acetylacetonate) iridium(III),
2,8-di-tert-butyl-5,11-bis(4-tert-butylphenyl)-6,12-diphenyltetracene,
bis(2-phenylbenzothiazolate)(acetylacetonate) iridium(III), platinum 5,10,15,20-tetraphenyltetrabenzoporphyrin,
osmium(II) bis(3-trifluoromethyl-5-(2-pyridine)pyrazolate) dimethylphenylphosphine,
osmium(II) bis(3-trifluoromethyl)-5-(4-tert-butylpyridyl)-1,2,4-triazolate)diphenyl-methylphosphine,
osmium(II) bis(3-(trifluoromethyl)-5-(2-pyridyl)-1,2,4-triazole)dimethylphenylphosphine,
osmium(II) bis(3-(trifluoromethyl)-5-(4-tert-butylpyridyl)-1,2,4-triazolate)dimethylphenylphosphine,
bis[2-(4-n-hexylphenyl)quinoline](acetylacetonate) iridium (III),
tris[2-(4-n-hexylphenyl)quinoline] iridium(III),
tris[2-phenyl-4-methylquinoline] iridium(III),
bis(2-phenylquinoline)(2-(3-methylphenyl)pyridinate) iridium(III),
bis(2-(9,9-diethylfluoren-2-yl)-1-phenyl-1H-benzo[d]imidazolato)(acetylacetonate) iridium(III),
bis(2-phenylpyridine)(3-(pyridin-2-yl)-2H-chromen-9-onate) iridium(III),
bis(2-phenylquinoline)(2,2,6,6-tetramethylheptane-3,5-dionate) iridium(III),
bis(phenylisoquinoline)(2,2,6,6-tetramethylheptane-3,5-dionate) iridium(III),
iridium(III) bis(4-phenylthieno[3,2-c]pyridinato-N,$C^2$) acetylacetonate,
(E)-2-(2-tertbutyl-6-(2-(2,6,6-trimethyl-2,4,5,6-tetrahydro-1H-pyrrolo[3,2,1-ij]quinolin-S-yl)vinyl)-4H-pyran-4-ylidene)malononitrile,
bis(3-trifluoromethyl-5-(1-isoquinolyl)pyrazolate)(methyldiphenylphosphine) ruthenium,
bis[(4-n-hexylphenyl)isoquinoline](acetylacetonate) iridium(III),
platinum(II) octaethylporphin,
bis(2-methyldibenzo[f,h]quinoxaline)(acetylacetonate) iridium(III) and
tris[(4-n-hexylphenyl)isoquinoline] iridium(III).

Specific examples of electron-transporting layer-forming materials include lithium 8-hydroxyquinolinate, 2,2',2''-(1,3,5-benzinetriyl)-tris(1-phenyl-1-1H-benzimidazole), 2-(4-biphenyl)-5-(4-tert-butylphenyl)-1,3,4-oxadiazole, 2,9-dimethyl-4,7-diphenyl-1,10-phenanthroline, 4,7-diphenyl-1,10-phenanthroline, bis(2-methyl-8-quinolinolate)-4-(phenylphenolato)aluminum,
1,3-bis[2-(2,2'-bipyridin-6-yl)-1,3,4-oxadiazo-5-yl]benzene,
6,6'-bis[5-(biphenyl-4-yl)-1,3,4-oxadiazo-2-yl]-2,2'-bipyridine,
3-(4-biphenyl)-4-phenyl-5-tert-butylphenyl-1,2,4-triazole,
4-(naphthalen-1-yl)-3,5-diphenyl-4H-1,2,4-triazole,
2,9-bis(naphthalen-2-yl)-4,7-diphenyl-1,10-phenanthroline,
2,7-bis[2-(2,2'-bipyridin-6-yl)-1,3,4-oxadiazo-5-yl]-9,9-dimethylfluorene,
1,3-bis[2-(4-tert-butylphenyl)-1,3,4-oxadiazo-5-yl]benzene,
tris(2,4,6-trimethyl-3-(pyridin-3-yl)phenyl)borane,
1-methyl-2-(4-(naphthalen-2-yl)phenyl)-1H-imidazo[4,5f][1,10]phenanthroline,
2-(naphthalen-2-yl)-4,7-diphenyl-1,10-phenanthroline, phenyldipyrenylphosphine oxide,
3,3',5,5'-tetra[(m-pyridyl)-phen-3-yl]biphenyl, 1,3,5-tris[(3-pyridyl)-phen-3-yl]benzene,
4,4'-bis(4,6-diphenyl-1,3,5-triazin-2-yl)biphenyl,
1,3-bis[3,5-di(pyridin-3-yl)phenyl]benzene, bis(10-hydroxybenzo[h]quinolinato)beryllium,
diphenylbis(4-(pyridin-3-yl)phenyl)silane and 3,5-di(pyren-1-yl)pyridine.

Examples of electron-injecting layer-forming materials include lithium oxide ($Li_2O$), magnesium oxide (MgO), alumina ($Al_2O_3$), lithium fluoride (LiF), sodium fluoride (NaF), magnesium fluoride ($MgF_2$), cesium fluoride (CsF), strontium fluoride ($SrF_2$), molybdenum trioxide ($MoO_3$), aluminum, lithium acetylacetonate (Li(acac)), lithium acetate and lithium benzoate.

Examples of cathode materials include aluminum, magnesium-silver alloys, aluminum-lithium alloys, lithium, sodium, potassium and cesium.

Another example is described below of a method for producing the organic EL device of the invention in a case where a thin film obtained from the charge-transporting varnish of the invention serves as the hole-injecting layer.

An organic EL device having a charge-transporting thin film formed with the charge-transporting varnish of the invention can be produced by, in the organic EL device production method described above, successively forming a hole-transporting layer and a light-emitting layer instead of carrying out vacuum evaporation operations for a hole-transporting layer, a light-emitting layer, an electron-transporting layer and an electron-injecting layer. Specifically, the charge-transporting varnish of the invention is applied onto an anode substrate, and a hole-injecting layer is formed by the above-described method. A hole-transporting layer and a light-emitting layer are then successively formed thereon, following which a cathode material is vapor-deposited on top, thereby giving an organic EL device.

The cathode and anode materials used here may be similar to those described above, and similar cleaning treatment and surface treatment may be carried out.

The method of forming the hole-transporting layer and the light-emitting layer is exemplified by a film-forming method that involves adding a solvent to a hole-transporting polymer material or a light-emitting polymer material, or to the material obtained by adding a dopant to either of these, thereby dissolving or uniformly dispersing the material, and then applying the solution or dispersion onto the hole-injecting layer or the hole-transporting layer and subsequently baking.

Examples of hole-transporting polymer materials include
poly[(9,9-dihexylfluorenyl-2,7-diyl)-co-(N,N'-bis{p-butylphenyl}-1,4-diaminophenylene)],
poly[(9,9-dioctylfluorenyl-2,7-diyl)-co-(N,N'-bis {p-butylphenyl}-1,1'-biphenylene-4,4-diamine)],
poly[(9,9-bis{1'-penten-5'-yl}fluorenyl-2,7-diyl)-co-(N,N'-bis{p-butylphenyl}-1,4-diaminophenylene)],
poly[N,N'-bis(4-butylphenyl)-N,N'-bis(phenyl)-benzidine] end-capped with polysilsesquioxane and
poly[(9,9-dioctylfluorenyl-2,7-diyl)-co-(4,4'-(N-(p-butylphenyl))diphenylamine)].

Examples of light-emitting polymer materials include polyfluorene derivatives such as poly(9,9-dialkylfluorene) (PDAF), poly(phenylene vinylene) derivatives such as poly (2-methoxy-5-(2'-ethylhexoxy)-1,4-phenylene vinylene) (MEH-PPV), polythiophene derivatives such as poly(3-alkylthiophene) (PAT), and polyvinylcarbazole (PVCz).

Exemplary solvents include toluene, xylene and chloroform. Examples of the method of dissolution or uniform dispersion include stirring, stirring under applied heat, and ultrasonic dispersion.

Examples of the method of application include, but are not particularly limited to, inkjet coating, spraying, dipping, spin coating, transfer printing, roll coating and brush coating. Application is preferably carried out in an inert gas atmosphere such as nitrogen or argon.

Examples of the baking method include methods that involve heating in an oven or on a hot plate, either within an inert gas atmosphere or in a vacuum.

An example is described below of a method for producing the organic EL device of the invention in cases where a thin film obtained from the charge-transporting varnish of the invention serves as a hole-injecting-and-transporting layer.

A hole-injecting-and-transporting layer is formed on an anode substrate. A light-emitting layer, an electron-transporting layer, an electron-injecting layer and a cathode are provided in this order on the hole-injecting-and-transporting layer. Methods of forming the light-emitting layer, electron-transporting layer and electron-injecting layer, and specific examples thereof, include the same as those mentioned above.

The anode material, the light-emitting layer, the light-emitting dopant, the materials which form the electron-transporting layer and the electron-blocking layer, and the cathode material are exemplified in the same way as mentioned above.

A hole-blocking layer, an electron-blocking layer or the like may be optionally provided between the electrodes and any of the above layers. By way of illustration, an example of a material that forms an electron-blocking layer is tris (phenylpyrazole)iridium.

The materials which make up the anode, the cathode and the layers formed therebetween differ according to whether a device provided with a bottom emission structure or a top emission structure is to be fabricated, and so are suitably selected while taking this into account.

Typically, in a device having a bottom emission structure, a transparent anode is used on the substrate side and light is extracted from the substrate side, whereas in a device having a top emission structure, a reflective anode made of metal is used and light is extracted from the transparent electrode (cathode) side in the opposite direction from the substrate. Hence, for example, with regard to the anode material, when fabricating a device having a bottom emission structure, a transparent anode of ITO or the like is used, and when fabricating a device having a top emission structure, a reflective anode of Al/Nd or the like is used.

To prevent deterioration of the device characteristics, the organic EL device of the invention may be sealed in the usual manner with, if necessary, a desiccant or the like.

EXAMPLES

Working Examples and Comparative Examples are given below to more concretely illustrate the invention, although the invention is not limited by these Examples. In the Examples, the following equipment was used for sample preparation and for analyzing physical properties.
(1) $^1$H-NMR Measurement: Ascend 500, from Bruker
(2) LC/MS: ZQ 2000, from Waters Corporation
(3) Substrate Cleaning: Substrate cleaning machine
  (reduced-pressure plasma system),
  from Choshu Industry Co., Ltd.
(4) Varnish Coating: MS-A100 Spin Coater, from Mikasa Co., Ltd.
(5) Film Thickness Measurement: Surfcorder ET-4000 microfigure measuring instrument, from Kosaka Laboratory, Ltd.
(6) Organic EL Device Fabrication: C-E2L1G1-N Multifunction Vapor Deposition System, from Choshu Industry Co., Ltd.
(7) Measurement of Organic EL Device Brightness:
  I-V-L Measurement System from Tech World, Inc.
(8) Measurement of Solvent Dielectric Constant:
  1260 Frequency Response Analyzer and
  1296 Dielectric Interface, both from Solartron
(9) Measurement of Varnish Conductivity:
  SevenGo SG3 conductivity meter
  from Mettler Toledo

[1] Synthesis of Sulfonic Acid Compounds

[Comparative Example 1-1] Synthesis of NSO-2

The sulfonic acid compound NSO-2 of the following formula was synthesized in accordance with the method described in WO 2006/025342.

[Chem. 17]

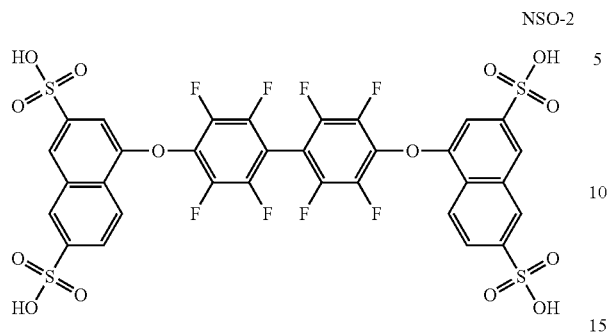

NSO-2

[Comparative Example 1-2] Synthesis of NSO-2-PGME

The sulfonic acid ester compound NSO-2-PGME of the following formula was synthesized in accordance with the method described in Patent Document 6.

[Chem. 18]

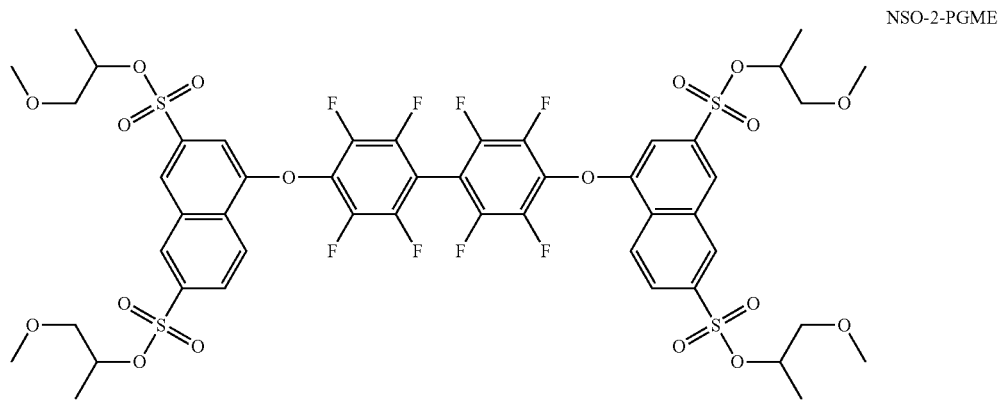

NSO-2-PGME

[Working Example 1-1] Synthesis of NSO-2-PGEE

The sulfonic acid ester compound NSO-2-PGEE was synthesized in accordance with the following reaction scheme.

[Chem. 19]

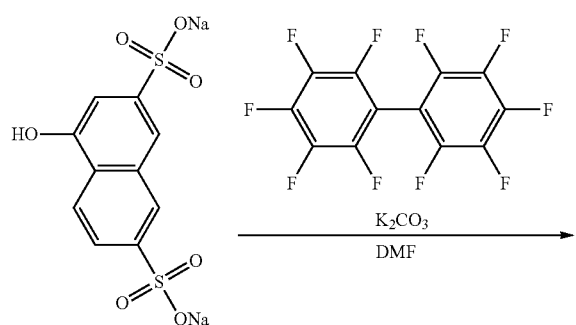

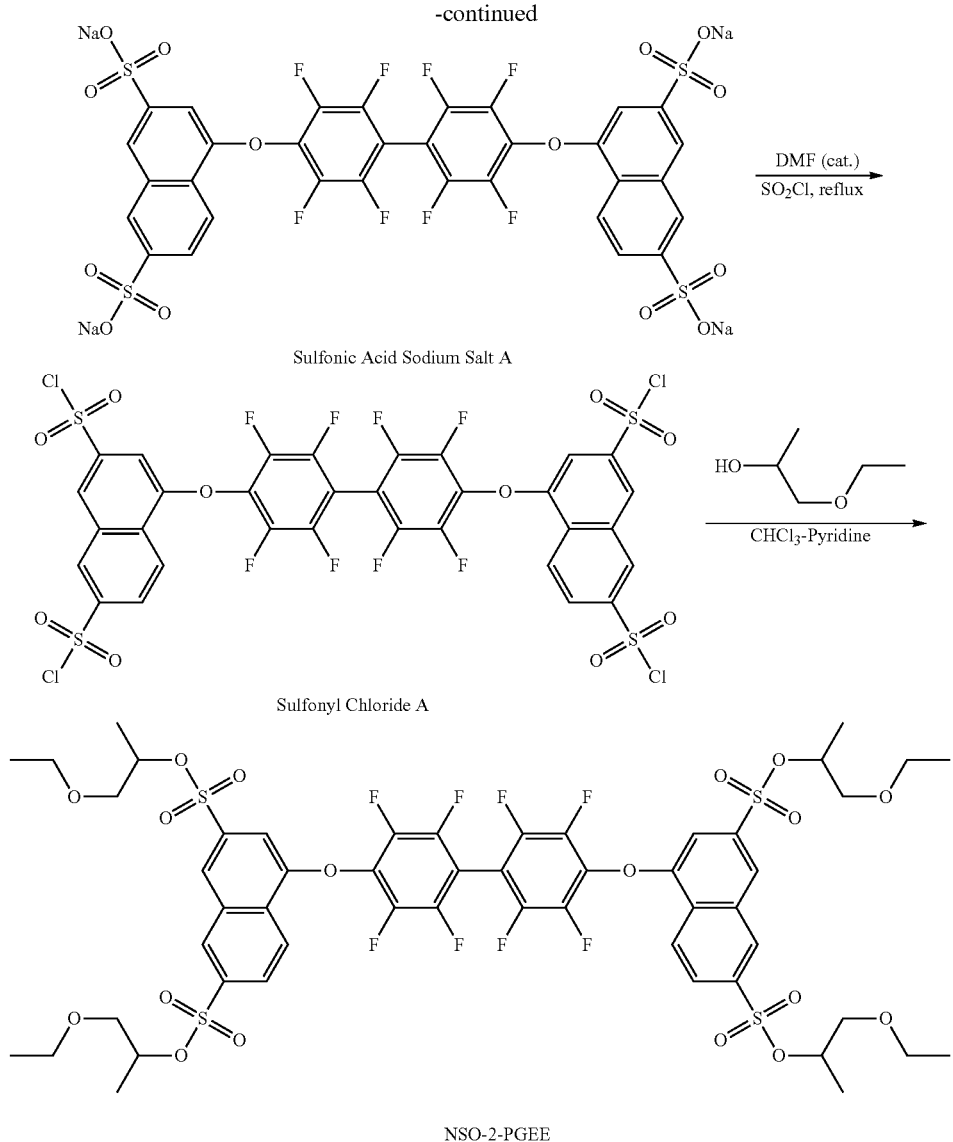

Under a nitrogen atmosphere, 4.8 g (14.36 mol) of perfluorobiphenyl, 4.2 g (30.15 mol) of potassium carbonate and 100 mL of N,N-dimethylformamide were successively added to 11 g (31.59 mmol) of sodium 1-naphthol-3,6-disulfonate, and the reaction system was flushed with nitrogen and subsequently stirred for 6 hours at an internal temperature of 100° C. The system was allowed to cool to room temperature, following which the potassium carbonate residue was removed by filtration and vacuum concentration was carried out. To remove the remaining impurities, 100 mL of methanol was added to the residue and stirring was carried out for 30 minutes at room temperature. The suspension was then filtered, giving 11.8 g (yield, 83%) of Sulfonic Acid Sodium Salt A.

Thionyl chloride (8 mL) and DMF (0.1 mL) were added to 2 g (2 mmol) of Sulfonic Acid Sodium Salt A and the system was refluxed under heating for one hour, following which the thionyl chloride was driven off, giving a solid containing Sulfonyl Chloride A. This compound was used in the next step without further purification.

Chloroform (12 mL) and pyridine (8 mL) were added to this solid, and 2.50 g (24 mmol) of propylene glycol monoethyl ether (Junsei Chemical Co., Ltd.) was added at 0° C. The temperature was raised to room temperature and 3 hours of stirring was carried out thereafter. The solvent was driven off following which water was added, extraction was carried out with ethyl acetate, and the organic layer was dried over sodium sulfate. After filtration and concentration, the resulting crude product was purified by silica gel column chromatography (hexane/ethyl acetate), giving 1.09 g of the sulfonic acid ester compound NSO-2-PGEE as a white solid (yield, 44% (2-step yield from Sulfonic Acid Sodium Salt A)). The results of $^1$H-NMR and LC/MS measurement are shown below.

$^1$H-NMR (500 MHz, CDCl$_3$) δ:

0.92-0.97 (m, 12H), 1.34 and 1.40 (a pair of d, J=6.5 Hz, 12H), 3.32-3.52 (m, 16H), 4.80-4.87 (m, 4H), 7.37 (s, 2H), 8.22 (d, J=8.5 Hz, 2H), 8.45 (s, 2H), 8.61 (d, J=8.5 Hz, 2H), 8.69 (s, 2H).

LC/MS: (ESI$^+$) m/z; 1264 (M+NH$_4$)$^+$

[Working Example 1-2] Synthesis of NSO-2-PGEE by Another Method

The sulfonic acid ester compound NSO-2-PGEE was synthesized in accordance with the following reaction scheme.

[Chem. 20]

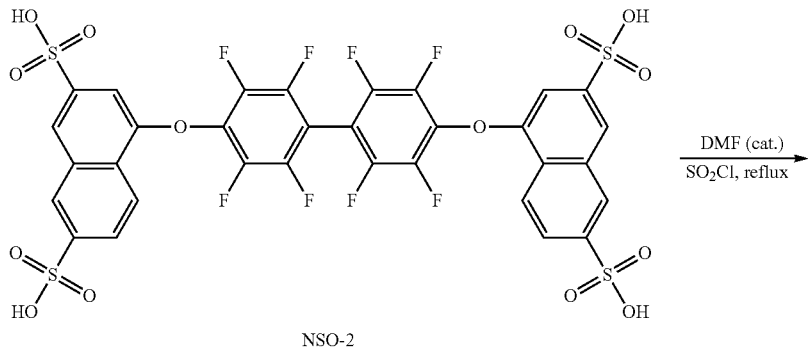

NSO-2

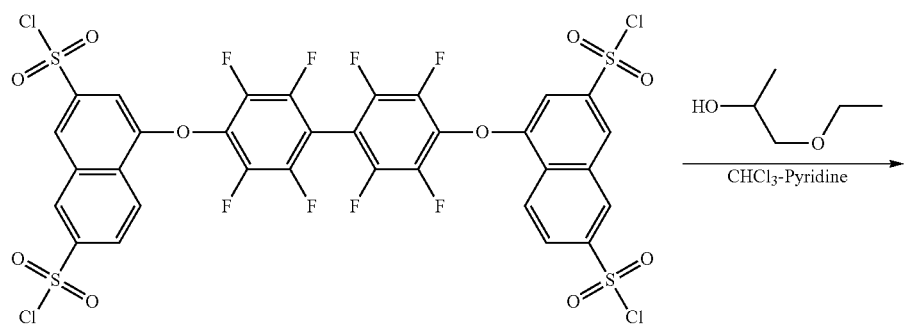

Sulfonyl Chloride A

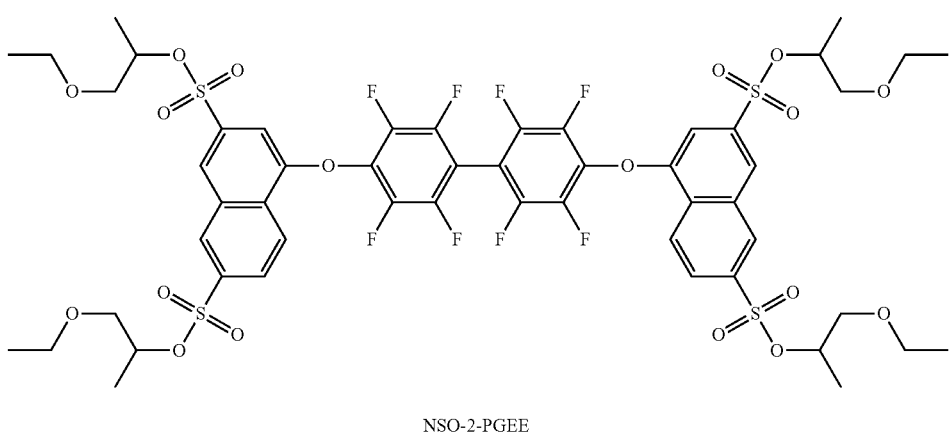

NSO-2-PGEE

Thionyl chloride (8 mL) and DMF (85 μL) were added to 2 g (2.2 mmol) of NSO-2 synthesized in Comparative Example 1-1 and the system was refluxed under heating for one hour, following which the thionyl chloride was driven off, giving a solid containing Sulfonyl Chloride A. This compound was used in the next step without further purification. Chloroform (12 mL) and pyridine (8 mL) were added to this solid, and 2.75 g (26.4 mmol) of propylene glycol monoethyl ether (Junsei Chemical Co., Ltd.) was added at 0° C. The temperature was raised to room temperature and 3 hours of stirring was carried out thereafter. The solvent was driven off, following which water was added, extraction was carried out with ethyl acetate, and the organic layer was dried over sodium sulfate. After filtration and concentration, the resulting crude product was purified by silica gel column chromatography (hexane/ethyl acetate), giving 1.50 g of the sulfonic acid ester compound NSO-2-PGEE as a white solid (yield, 54% (2-step yield from NSO-2)).

[Working Example 1-3] Synthesis of NSO-2-PGBE

Aside from using 3.17 g (24 mmol) of propylene glycol monobutyl ether instead of propylene glycol monoethyl ether, synthesis was carried out in the same way as in Working Example 1-1, thereby giving 0.25 g of the sulfonic acid ester compound NSO-2-PGBE having the formula shown below (yield, 9% (2-step yield from Sulfonic Acid Sodium Salt A)) as a white solid. The results of $^1$H-NMR and LC/MS measurement are shown below.

$^1$H-NMR (500 MHz, CDCl$_3$) δ:
0.75-0.82 (m, 12H), 1.12-1.41 (m, 28H), 3.26-3.50 (m, 16H), 4.79-4.91 (m, 4H), 7.36 (s, 2H), 8.22 (dd, J=1.5, 9.0 Hz, 2H), 8.44 (s, 2H), 8.61 (d, J=9.0 Hz, 2H), 8.68 (d, j=1.5 Hz, 2H).
LC/MS: (ESI$^+$) m/z; 1376 (M+NH$_4$)$^+$

[Chem. 21]

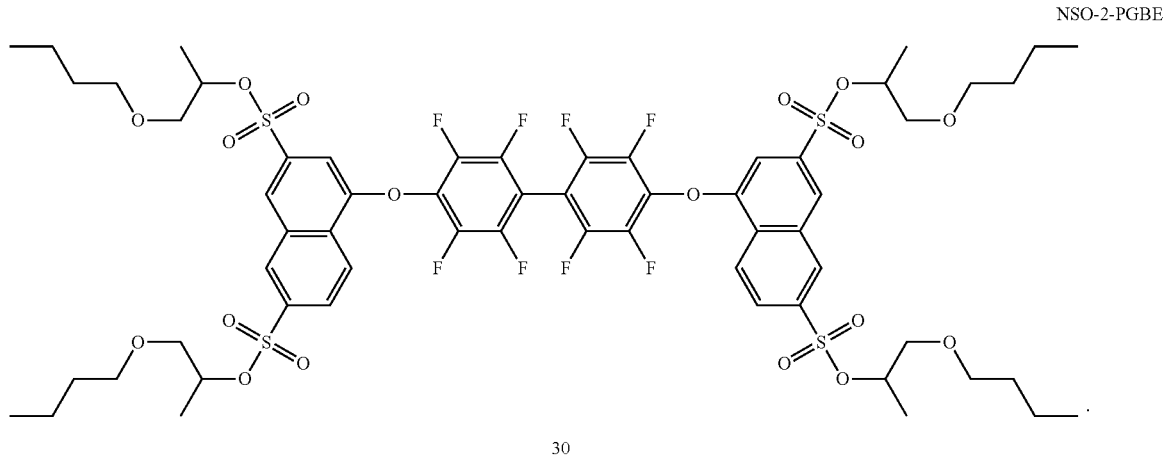

NSO-2-PGBE

[Working Example 1-4] Synthesis of NSO-2-POP

Aside from using 3.65 g (24 mmol) of propylene glycol monophenyl ether instead of propylene glycol monoethyl ether, synthesis was carried out in the same way as in Working Example 1-1, thereby giving 0.54 g of the sulfonic acid ester compound NSO-2-POP having the formula shown below (yield, 19% (2-step yield from Sulfonic Acid Sodium Salt A)) as a white solid. The results of $^1$H-NMR and LC/MS measurement are shown below.

$^1$H-NMR (500 MHz, CDCl$_3$) δ:
1.54-1.55 (m, 12H), 3.94-3.96 (m, 4H), 4.01-4.09 (m, 4H), 5.01-5.07 (m, 4H),
6.53-6.58 (m, 8H), 6.84-6.88 (m, 4H), 7.09-7.15 (m, 8H), 7.35 (s, 2H),
8.18 (d, J=9.0 Hz, 2H), 8.32 (s, 2H), 8.54-8.56 (m, 4H).
LC/MS: (ESI$^+$) m/z; 1456 (M+NH$_4$)$^+$

[Chem. 22]

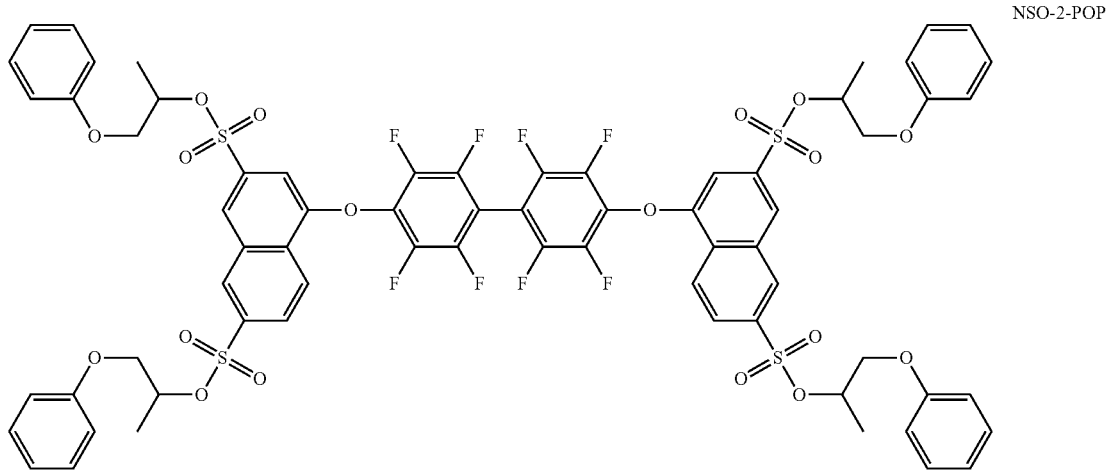

NSO-2-POP

[2] Preparation of Charge-Transporting Varnishes and Evaluation of Solubility

[Working Example 2-1] Preparation of Charge-Transporting Varnish A1 (Solids Concentration, 5 wt %)

The NSO-2-PGEE synthesized in Working Example 1-1 (385 mg) and Oligoaniline Compound 1 (141 mg) were added to a mixed solvent of 3-phenoxytoluene (5 g; dielectric constant, 2.7) and tetralin (5 g; dielectric constant, 2.2), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish A1. Oligoaniline Compound 1 was synthesized in accordance with the method described in WO 2013/084664.

[Chem. 23]

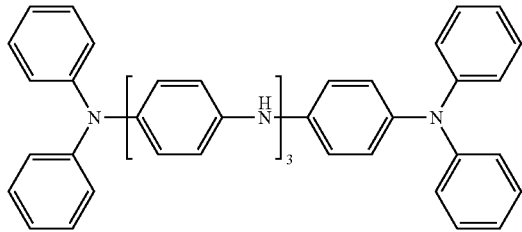

Oligoaniline Compound 1

[Working Example 2-2] Preparation of Charge-Transporting Varnish A2 (Solids Concentration, 2 wt %)

Aside from using the NSO-2-PGEE synthesized in Working Example 1-2 (149 mg) and Oligoaniline Compound 1 (55 mg), the varnish was prepared in the same way as in Working Example 2-1.

[Working Example 2-3] Preparation of Charge-Transporting Varnish A3 (Solids Concentration, 5 Wt %)

NSO-2-PGBE (394 mg) and Oligoaniline Compound 1 (132 mg) were added to a mixed solvent of 3-phenoxytoluene (5 g) and tetralin (5 g), and the system was stirred for 5 minutes under heating at 50° C. and 400 rpm. As a result, the NSO-2-PGBE dissolved completely in the solvent. The resulting solution was filtered using a PTFE filter having a pore size of 0.2 μm, giving Charge-Transporting Varnish A3.

[Working Example 2-4] Preparation of Charge-Transporting Varnish A4 (Solids Concentration, 5 wt %)

NSO-2-POP (399 mg) and Oligoaniline Compound 1 (127 mg) were added to a mixed solvent of 3-phenoxytoluene (5 g) and tetralin (5 g), and the system was stirred for 5 minutes under heating at 50° C. and 400 rpm. As a result, the NSO-2-POP dissolved completely in the solvent. The resulting solution was filtered using a PTFE filter having a pore size of 0.2 μm, giving Charge-Transporting Varnish A4.

[Working Example 2-5] Preparation of Charge-Transporting Varnish A5 (Solids Concentration, 5 wt %)

The NSO-2-PGEE synthesized in Working Example 1-2 (385 mg), Oligoaniline Compound 1 (85 mg) and Oligoaniline Compound 2 (56 mg) were added to a mixed solvent of 3-phenoxytoluene (5 g) and tetralin (5 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish A5. Oligoaniline Compound 2 was synthesized in accordance with the method described in Production Example 24-2 of WO 2015/050253.

[Chem. 24]

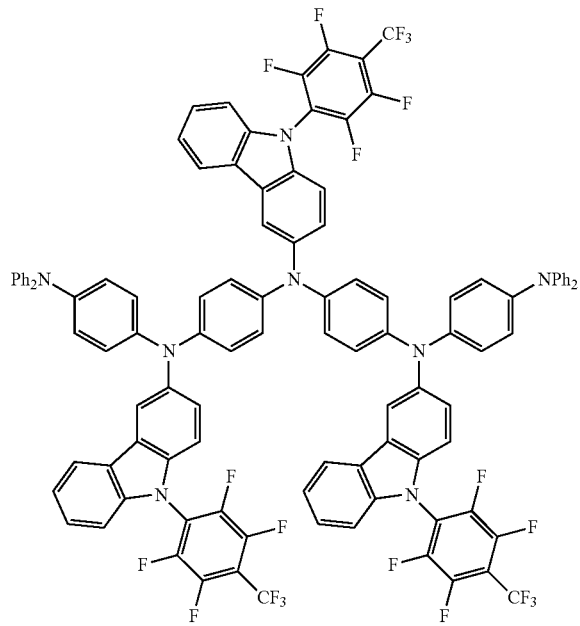

Oligoaniline Compound 2

[Working Example 2-6] Preparation of Charge-Transporting Varnish A6 (Solids Concentration, 5 wt %)

The NSO-2-PGEE synthesized in Working Example 1-2 (337 mg) and Oligoaniline Compound 3 (190 mg) were added to a mixed solvent of 3-phenoxytoluene (5 g) and tetralin (5 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 µm, giving Charge-Transporting Varnish A6. Oligoaniline Compound 3 was synthesized in accordance with the method described in Synthesis Example 18 of WO 2015/050253.

[Chem. 25]

Oligoaniline Compound 3

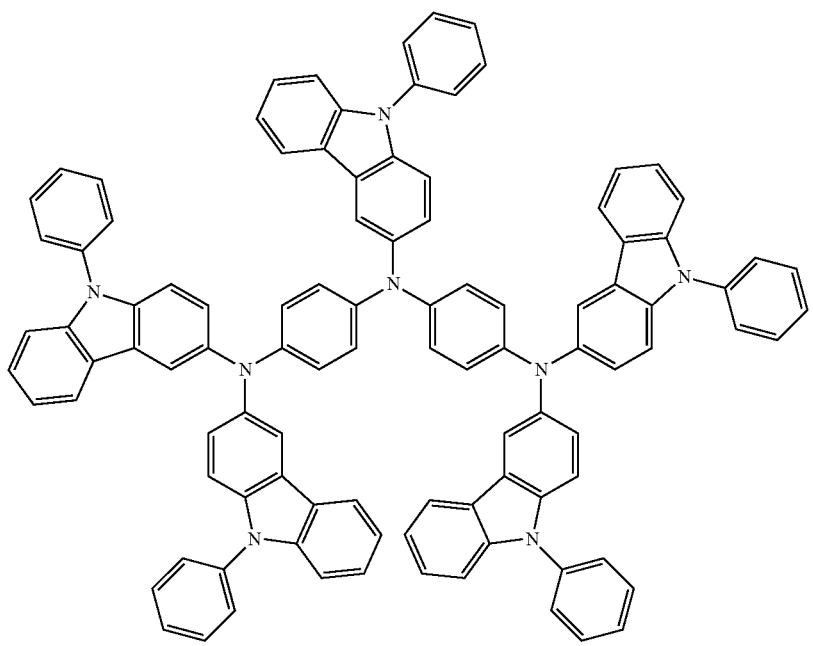

[Working Example 2-7] Preparation of Charge-Transporting Varnish A7 (Solids Concentration, 5 wt %)

The NSO-2-PGEE synthesized in Working Example 1-2 (329 mg), Oligoaniline Compound 2 (149 mg) and Oligoaniline Compound 3 (48 mg) were added to a mixed solvent of 3-phenoxytoluene (5 g) and tetralin (5 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 µm, giving Charge-Transporting Varnish A7.

[Working Example 2-8] Preparation of Charge-Transporting Varnish B1 (Solids Concentration, 5 wt %)

The NSO-2-PGEE synthesized in Working Example 1-2 (385 mg) and Oligoaniline Compound 1 (141 mg) were added to a mixed solvent of triethylene glycol butyl methyl ether (7 g; dielectric constant, 4.6) and butyl benzoate (3 g; dielectric constant, 2.5), and the system was stirred for 5 minutes under heating at 50° C. and 400 rpm. As a result, the NSO-2-PGEE dissolved completely in the solvent. The resulting solution was filtered using a PTFE filter having a pore size of 0.2 µm, giving Charge-Transporting Varnish B1.

[Working Example 2-9] Preparation of Charge-Transporting Varnish B2 (Solids Concentration, 5 wt %)

The NSO-2-PGEE synthesized in Working Example 1-2 (385 mg), Oligoaniline Compound 1 (85 mg) and Oligoaniline Compound 2 (56 mg) were added to a mixed solvent of triethylene glycol butyl methyl ether (7 g) and butyl benzoate (3 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 µm, giving Charge-Transporting Varnish B2.

[Working Example 2-10] Preparation of Charge-Transporting Varnish B3 (Solids Concentration, 5 wt %)

The NSO-2-PGEE synthesized in Working Example 1-2 (337 mg) and Oligoaniline Compound 3 (190 mg) were added to a mixed solvent of triethylene glycol butyl methyl ether (7 g) and butyl benzoate (3 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 µm, giving Charge-Transporting Varnish B3.

[Working Example 2-11] Preparation of Charge-Transporting Varnish B4 (Solids Concentration, 5 wt %)

The NSO-2-PGEE synthesized in Working Example 1-2 (329 mg), Oligoaniline Compound 2 (149 mg) and Oligoaniline Compound 3 (48 mg) were added to a mixed solvent of triethylene glycol butyl methyl ether (7 g) and butyl benzoate (3 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish B4.

[Working Example 2-12] Preparation of Charge-Transporting Varnish C1 (Solids Concentration, 5 wt %)

The NSO-2-PGEE synthesized in Working Example 1-2 (385 mg) and Oligoaniline Compound 1 (141 mg) were added to a mixed solvent of 4-methoxytoluene (7 g; dielectric constant, 2.9) and cyclohexylbenzene (3 g; dielectric constant, 2.0), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish C1.

[Working Example 2-13] Preparation of Charge-Transporting Varnish C2 (Solids Concentration, 5 wt %)

The NSO-2-PGEE synthesized in Working Example 1-2 (385 mg), Oligoaniline Compound 1 (85 mg) and Oligoaniline Compound 2 (56 mg) were added to a mixed solvent of 4-methoxytoluene (7 g) and cyclohexylbenzene (3 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish C2.

[Working Example 2-14] Preparation of Charge-Transporting Varnish C3 (Solids Concentration, 5 wt %)

The NSO-2-PGEE synthesized in Working Example 1-2 (337 mg) and Oligoaniline Compound 3 (190 mg) were added to a mixed solvent of 4-methoxytoluene (7 g) and cyclohexylbenzene (3 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish C3.

[Working Example 2-15] Preparation of Charge-Transporting Varnish C4 (Solids Concentration, 5 wt %)

The NSO-2-PGEE synthesized in Working Example 1-2 (329 mg), Oligoaniline Compound 2 (149 mg) and Oligoaniline Compound 3 (48 mg) were added to a mixed solvent of 4-methoxytoluene (7 g) and cyclohexylbenzene (3 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish C4.

[Working Example 2-16] Preparation of Charge-Transporting Varnish D1 (Solids Concentration, 5 wt %)

The NSO-2-PGEE synthesized in Working Example 1-2 (385 mg) and Oligoaniline Compound 1 (141 mg) were added to a mixed solvent of ethyl benzoate (7 g, dielectric constant, 4.0) and dibenzyl ether (3 g; dielectric constant, 3.3), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish D1.

[Working Example 2-17] Preparation of Charge-Transporting Varnish D2 (Solids Concentration, 5 wt %)

The NSO-2-PGEE synthesized in Working Example 1-2 (385 mg), Oligoaniline Compound 1 (85 mg) and Oligoaniline Compound 2 (56 mg) were added to a mixed solvent of ethyl benzoate (7 g) and dibenzyl ether (3 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish D2.

[Working Example 2-18] Preparation of Charge-Transporting Varnish D3 (Solids Concentration, 5 wt %)

The NSO-2-PGEE synthesized in Working Example 1-2 (337 mg) and Oligoaniline Compound 3 (190 mg) were added to a mixed solvent of ethyl benzoate (7 g) and dibenzyl ether (3 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish D3.

[Working Example 2-19] Preparation of Charge-Transporting Varnish D4 (Solids Concentration, 5 wt %)

The NSO-2-PGEE synthesized in Working Example 1-2 (352 mg), Oligoaniline Compound 3 (159 mg) and Oligoaniline Compound 4 (15 mg) were added to a mixed solvent of ethyl benzoate (7 g) and dibenzyl ether (3 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish D4. Oligoaniline Compound 4 was synthesized in accordance with the method described in Synthesis Example 1 of WO 2016/190326.

[Chem. 26]

Oligoaniline Compound 4

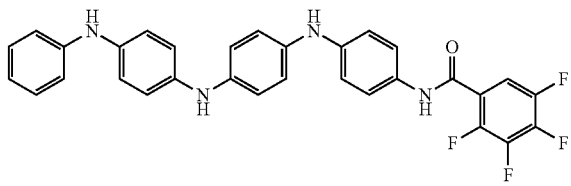

[Working Example 2-20] Preparation of Charge-Transporting Varnish D5 (Solids Concentration, 5 wt %)

The NSO-2-PGEE synthesized in Working Example 1-2 (329 mg), Oligoaniline Compound 2 (149 mg) and Oligoaniline Compound 3 (48 mg) were added to a mixed solvent of ethyl benzoate (7 g) and dibenzyl ether (3 g), and the system was stirred for 5 minutes under heating at 50° C. and 400 rpm. As a result, the NSO-2-PGEE dissolved completely in the solvent. The resulting solution was filtered using a PTFE filter having a pore size of 0.2 μm, giving Charge-Transporting Varnish D5.

[Comparative Example 2-1] Preparation of Charge-Transporting Varnish E (Solids Concentration, 5 wt %)

NSO-2-PGME (384 mg) and Oligoaniline Compound 1 (142 mg) were added to a mixed solvent of 3-phenoxytoluene (5 g) and tetralin (5 g), and the system was stirred for 30 minutes under heating at 50° C. and 400 rpm, but some material remained undissolved. With 20 minutes of stirring under heating at 70° C. and 400 rpm, the NSO-2-PGME completely dissolved in the solvent. The resulting solution was filtered using a PTFE filter having a pore size of 0.2 μm, giving Charge-Transporting Varnish E.

Comparative Example 2-2

NSO-2 (349 mg) and Oligoaniline Compound 1 (177 mg) were added to a mixed solvent of 3-phenoxytoluene (5 g) and tetralin (5 g), and the system was stirred for 30 minutes under heating at 90° C. and 400 rpm, but the NSO-2 did not dissolve whatsoever.

[Comparative Example 2-3] Preparation of Charge-Transporting Varnish F1 (Solids Concentration, 5 wt %)

NSO-2 (349 mg) and Oligoaniline Compound 1 (177 mg) were added to a mixed solvent of 1,3-dimethyl-2-imidazolidinone (3.3 g; dielectric constant, 26.0), 2,3-butanediol (4 g; dielectric constant, 17.0) and dipropylene glycol monomethyl ether (2.7 g; dielectric constant, 7.9), and the system was stirred for 5 minutes under heating at 50° C. and 400 rpm. As a result, the NSO-2 dissolved completely in the solvent. The resulting solution was filtered using a PTFE filter having a pore size of 0.2 μm, giving Charge-Transporting Varnish F1.

[Comparative Example 2-4] Preparation of Charge-Transporting Varnish F2 (Solids Concentration, 2 wt %)

Aside from using NSO-2 (149 mg) and Oligoaniline Compound 1 (55 mg), preparation was carried out in the same way as in Comparative Example 2-3.

[Comparative Example 2-5] Preparation of Charge-Transporting Varnish G (Solids Concentration, 5 wt %)

NSO-2-PGME (331 mg) and Oligoaniline Compound 3 (195 mg) were added to a mixed solvent of 3-phenoxytoluene (5 g) and tetralin (5 g), and the system was stirred for 30 minutes under heating at 50° C. and 400 rpm, but some material remained undissolved. With 20 minutes of stirring under heating at 70° C. and 400 rpm, the NSO-2-PGME completely dissolved in the solvent. The resulting solution was filtered using a PTFE filter having a pore size of 0.2 μm, giving Charge-Transporting Varnish G.

NSO-2-PGEE, NSO-2-PGBE and NSO-2-POP dissolved completely in a mixed solvent of the low-polarity solvents 3-phenoxytoluene and tetralin when stirred for 5 minutes under heating at 50° C. and 400 rpm, whereas 20 minutes of stirring under heating at 70° C. and 400 rpm was required to completely dissolve NSO-2-PGME in the above mixed solvent, and NSO-2 did not dissolve in this mixed solvent. That is, the sulfonic acid ester compounds of the invention had excellent solubilities in low-polarity solvents.

[3] Evaluation of Shelf Stability of Charge-Transporting Varnish

Working Examples 3-1 to 3-4, Comparative Example 3-1 and 3-2

Charge-Transporting Varnishes A1, A3, A4 and E were stored under refrigeration at 2° C., and were examined for the presence or absence of precipitate when the periods of time shown in Table 1 below had elapsed following the start of storage. The results are shown in Table 1.

TABLE 1

| Charge-transporting varnish | | Sulfonic acid ester compound | Presence/Absence of precipitate | | | |
|---|---|---|---|---|---|---|
| | | | 6 days | 30 days | 60 days | 400 days |
| Working Example 3-1 | A1 | NSO-2-PGEE | no | no | no | no |
| Working Example 3-2 | A3 | NSO-2-PGBE | no | no | no | no |
| Working Example 3-3 | A4 | NSO-2-POP | no | no | no | no |
| Comparative Example 3-1 | E | NSO-2-PGME | yes | — | — | — |

The changes in the varnish moisture content and varnish conductivity with 7 months of atmospheric exposure following ink production are shown in Table 2. Varnish F2 produced in Comparative Example 2-4 underwent a rise in moisture content over time and also exhibited an accompanying increase in conductivity. By contrast, Varnish A2 produced in Working Example 2-2 showed no change in either moisture content or conductivity, and thus can be understood as having an excellent atmospheric stability.

TABLE 2

| Charge-transporting varnish | Sulfonic acid (ester) compound | Moisture content (%) Initial | Moisture content (%) After 7 months | Varnish conductivity (μS/cm²) Initial | Varnish conductivity (μS/cm²) After 7 months |
|---|---|---|---|---|---|
| Working Example 3-4 | A2 | NSO-2-PGEE | 0.03 | 0.03 | 0.00 | 0.00 |
| Comparative Example 3-2 | F2 | NSO-2 | 0.7 | 5.4 | 88 | 144 |

As shown in Tables 1 and 2, the charge-transporting varnishes that included a sulfonic acid ester compound of the invention had excellent shelf stabilities.

[4] Fabrication of Top Layer Deposition-Type Hole-Only Devices (HOD) and Evaluation of Device Characteristics In the following Working Examples and Comparative Examples, a glass substrate with dimensions of 25 mm×25 mm×0.7 mm (t) and having ITO patterned on the surface to a film thickness of 150 nm was used as the ITO substrate. Prior to use, impurities on the surface were removed with an 02 plasma cleaning system (150 W, 30 seconds).

Working Example 4-1

Charge-Transporting Varnish A1 was applied onto the ITO substrate using a spin coater and was subsequently pre-baked at 120° C. for 1 minute in open air and then subjected to a main bake at 200° C. for 30 minutes, thereby forming a 30-nm thin film on the ITO substrate.

Using a vapor deposition system (degree of vacuum, $2.0×10^{-5}$ Pa), thin films of α-NPD and aluminum were successively deposited thereon, giving a hole-only device. Vapor deposition was carried out at a deposition rate of 0.2 nm/s. The thicknesses of the α-NPD thin film and the aluminum thin film were set to respectively 30 nm and 80 nm.

To prevent the device characteristics from deteriorating due to the influence of oxygen, moisture and the like in air, the hole-only device was sealed with sealing substrates, following which the characteristics were evaluated. Sealing was carried out by the following procedure.

The hole-only device was placed between sealing substrates in a nitrogen atmosphere having an oxygen concentration of 2 ppm or less and a dew point of not more than −85° C., and the sealing substrates were laminated together using an adhesive (MORESCO Moisture Cut WB90US(P), from Moresco Corporation). At this time, a desiccant (HD-071010W-40, from Dynic Corporation) was placed, together with the hole-only device, within the sealing substrates. The laminated sealing substrates were irradiated with UV light (wavelength, 365 nm; dosage, 6,000 mJ/cm²) and then annealed at 80° C. for one hour to cure the adhesive.

Working Example 4-2

Aside from using Charge-Transporting Varnish A3 instead of Charge-Transporting Varnish A1, a hole-only device was fabricated in the same way as in Working Example 4-1.

Working Example 4-3

Aside from using Charge-Transporting Varnish A4 instead of Charge-Transporting Varnish A1, a hole-only device was fabricated in the same way as in Working Example 4-1.

Comparative Example 4-1

Aside from using Charge-Transporting Varnish E instead of Charge-Transporting Varnish A1, a hole-only device was fabricated in the same way as in Working Example 4-1.

Comparative Example 4-2

Aside from using Charge-Transporting Varnish F instead of Charge-Transporting Varnish A1 and carrying out the pre-bake at 80° C. for 1 minute and the main bake at 230° C. for 15 minutes, a hole-only device was fabricated in the same way as in Working Example 4-1.

The current densities at a driving voltage of 3 V were measured for the hole-only devices fabricated in the above Working Examples and Comparative Examples. The results are shown in Table 3.

TABLE 3

| | Charge-transporting varnish | Current density (mA/cm²) |
|---|---|---|
| Working Example 4-1 | A1 | 960 |
| Working Example 4-2 | A3 | 914 |
| Working Example 4-3 | A4 | 1,070 |
| Comparative Example 4-1 | E | 771 |
| Comparative Example 4-2 | F1 | 1,170 |

As shown in Table 3, charge-transporting varnishes containing the sulfonic acid ester compounds of the invention exhibited hole transportabilities comparable to or better than those of conventional charge-transporting varnishes.

[5] Fabrication of Top Layer Deposition-Type Hole-Only Devices (HOD) and Evaluation of Device Characteristics (2)

The ITO substrate used in the following Working Examples and Comparative Examples was the same as that described above.

Working Example 5-1

Charge-Transporting Varnish A1 was applied onto the ITO substrate using a spin coater, following which it was pre-baked at 120° C. for 1 minute in open air and then subjected to a main bake at 230° C. for 15 minutes, thereby forming a 30-nm hole-injecting-layer thin film on the ITO substrate.

Next, in a glove box under a nitrogen atmosphere, a 0.6 wt % xylene solution of TFB polymer (LT-N148, from Luminescence Technology) was spin-coated onto the hole-injecting layer to form a film, and heating and baking at 130° C. was carried out for 10 minutes, thereby forming a 40-nm hole-transporting-layer thin-film.

Using a vapor deposition system (degree of vacuum, $2.0×10^{-5}$ Pa), a thin film of aluminum was deposited thereon, giving a hole-only device. Vapor deposition was carried out at a deposition rate of 0.2 nm/s. The thickness of the aluminum thin film was set to 80 nm.

To prevent the device characteristics from deteriorating due to the influence of oxygen, moisture and the like in air, the hole-only device was sealed with sealing substrates, following which the characteristics were evaluated. Sealing was carried out by the following procedure.

The hole-only device was placed between sealing substrates in a nitrogen atmosphere having an oxygen concentration of 2 ppm or less and a dew point of not more than −85° C., and the sealing substrates were laminated together using an adhesive (MORESCO Moisture Cut WB90US(P), from Moresco Corporation). At this time, a desiccant (HD-071010W-40, from Dynic Corporation) was placed, together with the hole-only device, within the sealing substrates. The laminated sealing substrates were irradiated with UV light (wavelength, 365 nm; dosage, 6,000 mJ/cm$^2$) and then annealed at 80° C. for one hour to cure the adhesive.

Working Examples 5-2 to 5-4

Aside from using Charge-Transporting Varnishes A5 to A7 instead of Charge-Transporting Varnish A1, hole-only devices were produced in the same way as in Working Example 5-1.

Working Examples 5-5 to 5-8

Aside from using Charge-Transporting Varnishes B1 to B4 instead of Charge-Transporting Varnish A1, hole-only devices were produced in the same way as in Working Example 5-1.

Working Examples 5-9 to 5-12

Aside from using Charge-Transporting Varnishes C1 to C4 instead of Charge-Transporting Varnish A1, hole-only devices were produced in the same way as in Working Example 5-1.

Working Examples 5-13 to 5-17

Aside from using Charge-Transporting Varnishes D1 to D5 instead of Charge-Transporting Varnish A1, hole-only devices were produced in the same way as in Working Example 5-1.

Comparative Example 5-1

Aside from not forming a hole-transporting layer, a hole-only device was produced in the same way as in Working Example 5-1.

Comparative Examples 5-2 to 5-4

Aside from using Charge-Transporting Varnish E, F1 or G instead of Charge-Transporting Varnish A1, hole-only devices were produced in the same way as in Working Example 5-1.

The current densities at a driving voltage of 5 V were measured for the hole-only devices fabricated in the foregoing Working Examples and Comparative Examples. The results are shown in Table 4.

TABLE 4

| | Charge-transporting varnish | Oligoaniline compound | Current density (mA/cm$^2$) |
|---|---|---|---|
| Working Example 5-1 | A1 | Compound 1 | 524 |
| Working Example 5-2 | A5 | Compounds 1, 2 | 1,633 |
| Working Example 5-3 | A6 | Compound 3 | 1,840 |
| Working Example 5-4 | A7 | Compounds 2, 3 | 2,025 |
| Working Example 5-5 | B1 | Compound 1 | 228 |
| Working Example 5-6 | B2 | Compounds 1, 2 | 1,150 |
| Working Example 5-7 | B3 | Compound 3 | 2,188 |
| Working Example 5-8 | B4 | Compounds 2, 3 | 1,725 |
| Working Example 5-9 | C1 | Compound 1 | 424 |
| Working Example 5-10 | C2 | Compounds 1, 2 | 1,540 |
| Working Example 5-11 | C3 | Compound 3 | 2,167 |
| Working Example 5-12 | C4 | Compounds 2, 3 | 2,115 |
| Working Example 5-13 | D1 | Compound 1 | 475 |
| Working Example 5-14 | D2 | Compounds 1, 2 | 1,438 |
| Working Example 5-15 | D3 | Compound 3 | 2,240 |
| Working Example 5-16 | D4 | Compounds 3, 4 | 2,298 |
| Working Example 5-17 | D5 | Compounds 2, 3 | 1,628 |
| Comparative Example 5-1 | — | — | 49 |
| Comparative Example 5-2 | E | Compound 1 | 164 |
| Comparative Example 5-3 | F1 | Compound 1 | 831 |
| Comparative Example 5-4 | G | Compound 3 | 1,213 |

As shown in Table 4, by using a charge-transporting varnish containing a sulfonic acid ester compound of the invention to form a hole-injecting layer, the HOD improves compared with when a hole-injecting layer is not used (Comparative Example 5-1). Moreover, in cases where the oligoaniline compound used is the same, the use of a charge-transporting varnish containing a sulfonic acid ester compound of the invention to form a hole-injecting layer results in each instance in a higher HOD current than when a charge-transporting varnish containing a conventional sulfonic acid ester compound or sulfonic acid compound is used to form the hole-injecting layer.

[6] Fabrication of Organic EL Devices and Evaluation of Device Characteristics

In the following Working Examples and Comparative Examples, a glass substrate with dimensions of 25 mm×25 mm×0.7 mm (t) and having ITO patterned on the surface to a film thickness of 150 nm was used as an ITO substrate. Prior to use, impurities on the surface were removed with an $O_2$ plasma cleaning system (150 W, 30 seconds).

Working Example 6-1

Charge-Transporting Varnish A1 was applied onto the ITO substrate using a spin coater and was subsequently dried at 120° C. for 1 minute and then, in open air, baked at 200° C. for 30 minutes, thereby forming a uniform 30-nm thin film on the ITO substrate.

Next, using a vapor deposition system (degree of vacuum, 1.0×10$^{-5}$ Pa), 30 nm of α-NPD was deposited at a rate of 0.2 nm/s onto the ITO substrate where the thin film was formed, following which CBP and Ir(ppy)$_3$ were co-deposited. Co-deposition was carried out by controlling the rate of deposition such that the concentration of Ir(ppy)$_3$ becomes 6%, to a thickness of 40 nm. Thin films of Alq$_3$, lithium fluoride and aluminum were then successively deposited, thereby giving an organic EL device. At this time, vapor deposition was carried out at a rate of 0.2 nm/s for Alq$_3$ and aluminum, and at a rate of 0.02 nm/s for lithium fluoride. The film thicknesses were set to, respectively, 20 nm, 0.5 nm and 80 nm.

To prevent the device characteristics from deteriorating due to the influence of oxygen, moisture and the like in air, the organic EL device was sealed with sealing substrates, following which the characteristics were evaluated. Sealing was carried out in the same way as described above.

Working Example 6-2

Aside from using Charge-Transporting Varnish A3 instead of Charge-Transporting Varnish A1, an organic EL device was fabricated in the same way as in Working Example 6-1.

Working Example 6-3

Aside from using Charge-Transporting Varnish A4 instead of Charge-Transporting Varnish A1, an organic EL device was fabricated in the same way as in Working Example 6-1.

Comparative Example 6-1

Aside from using Charge-Transporting Varnish E instead of Charge-Transporting Varnish A1, an organic EL device was fabricated in the same way as in Working Example 6-1.

Comparative Example 6-2

Aside from using Charge-Transporting Varnish F1 instead of Charge-Transporting Varnish A1 and carrying out the pre-bake at 80° C. for 1 minute and the main bake at 230° C. for 15 minutes, an organic EL device was fabricated in the same way as in Working Example 6-1.

The voltages and current efficiencies at a brightness of 1,000 cd/m² were measured for these devices. The results are shown in Table 5. The size of the light-emitting surface on each device was 2 mm×2 mm.

TABLE 5

| | Charge-transporting varnish | Voltage (V) | Current density (cd/A) |
|---|---|---|---|
| Working Example 6-1 | A1 | 7.62 | 14.45 |
| Working Example 6-2 | A3 | 7.67 | 14.79 |
| Working Example 6-3 | A4 | 7.60 | 13.80 |
| Comparative Example 6-1 | E | 7.67 | 14.66 |
| Comparative Example 6-2 | F1 | 7.66 | 14.48 |

As shown in Table 5, charge-transporting varnishes containing sulfonic acid ester compounds of the invention exhibited organic EL characteristics comparable to those of conventional charge-transporting varnishes.

The invention claimed is:

1. An electron-accepting substance precursor consisting of a sulfonic acid ester compound of formula (1) below

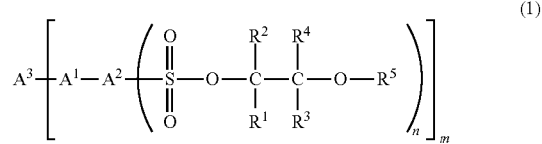

wherein $R^1$ to $R^4$ are each independently a hydrogen atom or a linear or branched alkyl group of 1 to 6 carbon atoms, and $R^5$ is a monovalent hydrocarbon group of 2 to 20 carbon atoms which may be substituted;
$A^1$ represents —O— or —S—, $A^2$ is a group having a valence of n+1 which is derived from naphthalene or anthracene, and $A^3$ is an m-valent group derived from perfluorobiphenyl; and
m is an integer that satisfies the condition $2 \le m \le 4$, and n is an integer that satisfies the condition $1 \le n \le 4$.

2. The electron-accepting substance precursor of claim 1, wherein $R^1$ or $R^3$ is a linear alkyl group of 1 to 3 carbon atoms and the remainder of $R^1$ to $R^4$ are hydrogen atoms.

3. The electron-accepting substance precursor of claim 2, wherein $R^1$ is a linear alkyl group of 1 to 3 carbon atoms and $R^2$ to $R^4$ are hydrogen atoms.

4. The electron-accepting substance precursor of any one of claims 1 to 3, wherein $R^5$ is a linear alkyl group of 2 to 4 carbon atoms or a phenyl group.

5. The electron-accepting substance precursor of claim 1, wherein m is 2.

6. The electron-accepting substance precursor of claim 1, wherein n is 2.

7. A charge-transporting varnish comprising the electron-accepting substance precursor of claim 1, a charge-transporting substance and an organic solvent.

8. The charge-transporting varnish of claim 7, wherein the organic solvent is a low-polarity organic solvent.

9. The charge-transporting varnish of claim 7 or 8, wherein the charge-transporting substance is an aniline derivative.

10. A charge-transporting thin film produced using the charge-transporting varnish of claim 7.

11. An organic electroluminescent device comprising the charge-transporting thin film of claim 10.

* * * * *